(12) United States Patent
Yokogawa et al.

(10) Patent No.: US 8,343,428 B2
(45) Date of Patent: Jan. 1, 2013

(54) MICROCHIP AND METHOD OF USING THE SAME

(75) Inventors: Akinori Yokogawa, Kyoto (JP); Toshihiro Mori, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 1007 days.

(21) Appl. No.: 12/257,589

(22) Filed: Oct. 24, 2008

(65) Prior Publication Data
US 2009/0111675 A1 Apr. 30, 2009

(30) Foreign Application Priority Data

| Oct. 29, 2007 | (JP) | ................................ 2007-280351 |
| Nov. 1, 2007 | (JP) | ................................ 2007-285039 |
| Nov. 1, 2007 | (JP) | ................................ 2007-285040 |

(51) Int. Cl.
*G01N 33/48* (2006.01)
*G01N 21/00* (2006.01)
*G01N 1/00* (2006.01)
*F15C 1/06* (2006.01)
*B01L 3/00* (2006.01)
*G01N 9/30* (2006.01)

(52) U.S. Cl. ...... 422/82.05; 422/68.1; 422/72; 422/502; 422/504; 422/506; 73/64.56; 137/803; 137/823; 137/833; 356/39

(58) Field of Classification Search .................. None
See application file for complete search history.

(56) References Cited

U.S. PATENT DOCUMENTS

| 3,798,459 A | * | 3/1974 | Anderson et al. ............. 250/576 |
| 3,899,296 A | * | 8/1975 | Mailen et al. .................... 422/50 |
| 4,814,282 A | | 3/1989 | Holen et al. |
| 5,122,284 A | * | 6/1992 | Braynin et al. ............... 210/782 |
| 7,749,444 B2 | * | 7/2010 | Yamada et al. ................. 422/81 |
| 2006/0008381 A1 | | 1/2006 | Taguchi et al. |
| 2007/0212259 A1 | * | 9/2007 | Fujimura et al. ............... 422/61 |
| 2008/0156079 A1 | | 7/2008 | Momose et al. |
| 2008/0296734 A1 | | 12/2008 | Momose |
| 2009/0084738 A1 | | 4/2009 | Momose |
| 2009/0098658 A1 | * | 4/2009 | Momose et al. ............. 436/164 |
| 2009/0104077 A1 | | 4/2009 | Momose |
| 2009/0135407 A1 | | 5/2009 | Kageyama et al. |

(Continued)

FOREIGN PATENT DOCUMENTS

JP 60-238761 11/1985

(Continued)

OTHER PUBLICATIONS

U.S. Appl. No. 12/467,404, filed May 18, 2009.

(Continued)

*Primary Examiner* — Sam P Siefke
*Assistant Examiner* — Jennifer Wecker
(74) *Attorney, Agent, or Firm* — Fish & Richardson P.C.

(57) ABSTRACT

A microchip including a first substrate with a groove formed on a substrate surface or a pass-through hole passing in a thickness direction of the substrate, and one or more second substrates laminated on a surface of the first substrate; the microchip including an optical measurement cuvette consisting of a space configured by the groove or the pass-through hole, and a substrate surface of the second substrate; wherein a side wall surface of the second substrate is positioned on an inner side than a side wall surface of the first substrate in at least one part of a side wall surface of the microchip, and a method of using the same are provided.

6 Claims, 16 Drawing Sheets

U.S. PATENT DOCUMENTS

| | | |
|---|---|---|
| 2009/0142232 A1 | 6/2009 | Okada et al. |
| 2009/0155125 A1 | 6/2009 | Michiue et al. |
| 2009/0232708 A1 | 9/2009 | Yokogawa et al. |

FOREIGN PATENT DOCUMENTS

| | | |
|---|---|---|
| JP | 2004-085506 | 3/2004 |
| JP | 2004-150804 | 5/2004 |
| JP | 2005-127771 | 5/2005 |
| JP | 2006-110491 | 4/2006 |
| JP | 2007-010435 | 1/2007 |
| JP | 2007-024851 | 2/2007 |
| WO | 2007/001084 | 1/2007 |

OTHER PUBLICATIONS

U.S. Appl. No. 12/424,913, filed Apr. 16, 2009.

Japanese Office Action for Japanese Patent Application No. 2007-285039 (mailed Jun. 12, 2012) with English translation.

Japanese Office Action for Japanese Patent Application No. 2007-285040 ( dated Jun. 12, 2012) with English translation.

Japanese Office Action for JP Application No. 2007-280351 dated Feb. 21, 2012, with English translation.

* cited by examiner

330 — 331b 311 331a

311

THICKNESS DIRECTION

MICROCHIP AND METHOD OF USING THE SAME

BACKGROUND OF THE INVENTION

1. Field of the Invention

The present invention relates to a microchip useful as a μ-TAS (Micro Total Analysis System) suitably used in a biochemical examination of DNA, protein, cell, immunity, blood and the like, chemical synthesis, as well as environmental analysis, and a method of using the same.

2. Description of the Background Art

Recently, in the fields of medical care and health, food product, drug discovery, and the like, the importance of sensing, detecting, and quantifying the biological material such as DNA (Deoxyribo Nucleic Acid) and enzyme, antigen, antibody, protein, virus, cells as well as chemical substance is increasing, and various biochips and micro-chemical chips (hereinafter collectively referred to as microchip) capable of easily and conveniently measuring the above have been proposed. As a series of experiments and analyzing operations performed in laboratories can be conducted in a chip of a few cm to 10 cm squares and about a thickness of a few mm to a few cm, the microchip has numerous advantages in that only a very small amount of specimen and reagent is necessary, the cost is low, the reaction speed is fast, a high throughput examination can be carried out, and the examination result can be immediately obtained at the specimen obtained site.

The microchip normally has a fluid circuit therein. The fluid circuit is mainly configured by, for example, each portion of a liquid reagent holding portion for holding a liquid reagent to mix or react with a specimen (blood by way of example), or to process the specimen, a measuring portion for measuring the specimen or the liquid reagent, a mixing portion for mixing the specimen and the liquid reagent, an optical measurement cuvette (detecting portion) for analyzing and/or examining the obtained mixed liquid, and a fine fluid path (e.g., fluid path having a width of about a few hundred μm) appropriately connecting each portion. The microchip is typically used by being mounted on a device (centrifugal device) capable of applying a centrifugal force thereto. The measurement and the mixing of the specimen and the liquid reagent, as well as, the introduction of the mixed liquid to the optical measurement cuvette can be carried out by applying the centrifugal force in an appropriate direction to the microchip. The examinations/analyses (e.g., detection of a specific component in the mixed liquid) of the mixed liquid introduced to the optical measurement cuvette (detecting portion) can be carried out by, for example, irradiating the optical measurement cuvette accommodating the mixed liquid with a detection light, and measuring the transmittance and the like thereof. The optical measurement cuvette accommodating the mixed liquid can be irradiated with the detection light from an angle substantially perpendicular to a surface of the microchip, and the like.

Thus, through the use of the microchip, the experiment, analysis and the like can be carried out with an extremely small amount of solution compared to the conventional experiment and analysis system using a pump, a pipette, a stirrer, and the like. However, since the handling amount of liquid is extremely small or less than or equal to a few tens μL in the experiments and the analyses using the microchip, a cross-sectional diameter of the optical measurement cuvette needs to be made small in order to perform the optical measurement of such small amount of liquid. In the conventional microchip, it is sometimes difficult to accurately align the optical measurement cuvette with an optical axis of the detection light. In particular, in the microchip where the liquid movement and the like in the fluid circuit is controlled using the centrifugal force, the microchip sometimes slightly move inside a microchip mounting portion of the centrifugal device due to the centrifugal force, and the above problem becomes significant. When using the centrifugal device in which a centrifugal force applying means and an optical measurement means are integrated, and a light source position itself cannot be moved, the alignment with the optical axis cannot carried out by fine tuning the light source position, and thus the microchip itself needs to have a structure capable of accurately aligning with the optical axis.

Furthermore, in the examinations and analyses using the microchip, especially the microchip capable of conducting examinations and analyses on plural items for one type of specimen introduced to the microchip (in this case, the microchip includes a plurality of optical measurement cuvettes), an easy and rapid detecting operation is desired to maximize the above merits of the microchip.

The centrifugal device (centrifugal force applying device) for applying the centrifugal force to the microchip normally includes a first circular stage that freely rotates (revolves) with a center point as the axis, where a microchip mounting portion composed of a groove having substantially the same shape as an outer shape of the microchip or a microchip fixing wall arranged along substantially the same shape as the outer shape of the microchip or the like is formed to incorporate the microchip on a surface of the first circular stage or on a surface of a second circular stage for rotating the microchip arranged on the first circular stage. After fitting the microchip into a region surrounded by the grooves or the walls, the first circular stage is rotated, and the centrifugal force is applied in an appropriate direction on the microchip while adjusting the orientation of the microchip by rotating the second circular stage as necessary.

It is very important to install the microchip in a correct orientation when fitting the microchip in the microchip mounting portion of the centrifugal device. If the microchip is fitted with the front and the back reversed, the liquid cannot be moved to the desired portion by the predetermined centrifugal operation. If the fluid path configuring the optical measurement cuvette (detecting portion) described above is not formed at a center position with respect to a thickness direction of the microchip, and is formed slightly shifted to the front or the back side of the microchip, the fluid path position and the light source position of the detection light shift if the microchip is fitted with the front and the back reversed, and the mixed liquid cannot be analyzed.

FIG. 26 is a schematic top view showing an outer shape of a conventional microchip described in Japanese Patent Laying-Open No. 2007-010435. As shown in FIG. 26, the conventional microchip has a symmetry plane A at the outer shape. If there is such symmetry plane or symmetry center, a problem in that the orientation (front and back etc.) of the microchip is easily mistaken arises when fitting the microchip to the centrifugal device. Further, the microchip is fabricated by laminating normally about two or three substrates, but a problem in that the orientation of the substrate tends to be easily mistaken arises when laminating the substrates in manufacturing the microchip.

SUMMARY OF THE INVENTION

As a solution to the problem in that it is difficult to accurately align the optical measurement cuvette with the optical axis of the detection light, consideration is made in increasing the cross-sectional area of the optical measurement cuvette to be irradiated with the detection light and facilitating the alignment of the optical axis. However, with this method, the amount of liquid to be introduced to the optical measurement cuvette needs to be increased, and the merits of using the microchip decrease.

The present invention is provided in view of solving the problems of the conventional microchip described above. In other words, it is an object of the present invention to provide a microchip capable of accurately aligning the optical measurement cuvette with the optical axis, and a method of using the same.

It is another object of the present invention to provide a microchip capable of easily and rapidly performing examinations/analyses on the examining/analyzing object (e.g., mixed liquid of specimen and liquid reagent) accommodated in a plurality of optical measurement cuvettes of the microchip.

It is another further object of the present invention to provide a microchip where the outer shape does not have a symmetry plane and the symmetry center, and where the orientation of the microchip or the substrate configuring the microchip is not mistaken when fitting the microchip to the centrifugal device or when laminating the substrates in manufacturing the microchip.

According to one aspect of the present invention, there is provided a microchip including a first substrate with a groove formed on a substrate surface or a pass-through hole passing in a thickness direction of the substrate, and one or more second substrates laminated on a surface of the first substrate, the microchip including an optical measurement cuvette consisting of a space configured by the groove or the pass-through hole, and a substrate surface of the second substrate; wherein a side wall surface of the second substrate is positioned on an inner side than a side wall surface of the first substrate in at least one part of a side wall surface of the microchip. The side wall surface of the second substrate may be positioned on the inner side than the side wall surface of the first substrate in all the side wall surfaces of the microchip.

In the microchip of the present invention described above, the substrate surface of the second substrate is preferably smaller than the substrate surface of the first substrate.

The side wall surface of the first substrate in at least one part of the side wall surface of the microchip in which the side wall surface of the second substrate is positioned on the inner side than the side wall surface of the first substrate preferably does not have a projection on the surface and more preferably is a plane.

The present invention provides a method of using the above microchip. The method of using the microchip of the present invention includes mounting the microchip in a device capable of applying a centrifugal force on the microchip and including a portion for mounting the microchip; and applying the centrifugal force in one or more directions on the microchip mounted on the device. A direction of the centrifugal force applied the last on the microchip is a direction the side wall surface of the microchip in which the side wall surface of the second substrate is positioned on an inner side than the side wall surface of the first substrate is pressed against an inner wall surface of the portion for mounting the microchip.

In the microchip of the present invention described above, at least one part of the side wall surface of the first substrate including the groove or the pass-through hole mainly configuring the optical measurement cuvette is configured so as to be positioned on the outer side of the side wall surface of the second substrate to be laminated (i.e., so that at least one part of the side wall surface of the first substrate projects out). According to the microchip of such configuration, the alignment precision of the optical axis of the detection light with the optical measurement cuvette in the optical measurement can be enhanced. In other words, the centrifugal force is applied on the microchip in such manner that the direction of the centrifugal force applied the last on the microchip is the direction the projecting side wall surface of the first substrate of the microchip is pressed against the fixed surface (inner wall surface) in the microchip mounting portion of the centrifugal device, so that the distance from the fixed surface to the optical measurement cuvette when irradiating the optical measurement cuvette with the detection light can be adjusted to an appropriate distance, and the alignment precision of the optical axis of the detection light with the optical measurement cuvette in the optical measurement can be enhanced.

According to another aspect of the present invention, there is provided a microchip interiorly including a fluid circuit, the microchip including a first substrate with a groove formed on a substrate surface and a plurality of pass-through holes passing in a thickness direction of the substrate, and one or more second substrates laminated on a surface of the first substrate; wherein the fluid circuit includes two or more optical measurement cuvettes consisting of a space configured by one pass-through hole of the plurality of pass-through holes and a substrate surface of the second substrate; and the two or more pass-through holes configuring the optical measurement cuvettes are arranged on a circumference of a same circle at a surface of the first substrate.

The fluid circuit preferably includes a liquid reagent holding portion for accommodating a liquid reagent; one or more measuring portions for measuring the liquid reagent or a specimen; and one or more overflow liquid accommodating portions, connected to the measuring portion, for accommodating the liquid reagent or the specimen overflowed from the measuring portion when measuring the liquid reagent or the specimen; where the overflow liquid accommodating portion is arranged on a circumference arranged with the two or more pass-through holes at the surface of the first substrate.

The fluid circuit may include one or more liquid reagent measuring portions for measuring the liquid reagent; one or more specimen measuring portions for measuring the specimen; two or more overflow liquid accommodating portions for accommodating the liquid reagent or the specimen overflowed from the liquid reagent measuring portion or the specimen measuring portion when measuring the liquid reagent or the specimen.

The microchip of the present invention is preferably a microchip including a first substrate with a groove formed on both surfaces of the substrate and a plurality of pass-through holes passing in the thickness direction of the substrate, and two second substrates laminated on both surfaces of the first substrate, the microchip interiorly including a fluid circuit of two layers arranged at different positions with respect to a thickness direction of the microchip.

The second substrate is preferably a transparent substrate. The first substrate is preferably an opaque substrate and more preferably a black substrate.

The microchip of the present invention described above includes a plurality of optical measurement cuvettes arranged on a circumference of the same circle. According to such a microchip of the present invention, examinations and analyses of multiple items can be conducted on one type of specimen, and the plurality of optical measurements in the examinations and analyses of the multiple items can be easily and rapidly conducted.

According to another further aspect of the present invention, there is provided a microchip consisting of a stacked body of at least two substrates, wherein a cutout is formed at any one of the corners at an outer edge of the microchip. The cutout may be formed from one surface to the other surface of the microchip.

The corner including the cutout is preferably a corner positioned on an upstream side in a centrifugal direction of a centrifugal force applied first on the microchip of the corners of the microchip.

Preferably, at least one of the substrates is a transparent substrate, and an adjacent substrate is a colored substrate.

The microchip of the present invention described above includes a cutout at the corner, and does not have a symmetry plane and the symmetry center at the outer shape, and thus the orientation of the microchip or the substrate configuring the same will not be mistaken when fitting the microchip in the centrifugal device or when laminating the substrates in manufacturing the microchip.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

First Embodiment

Figure 1:
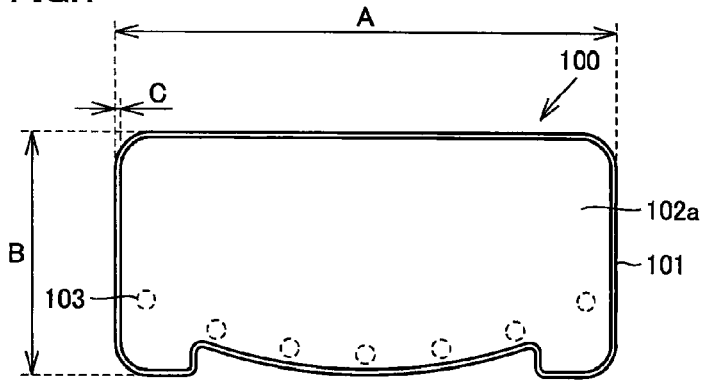
FIG. 1 is a schematic top view showing one example of a microchip according to a first embodiment of the present invention.
Figure 2:
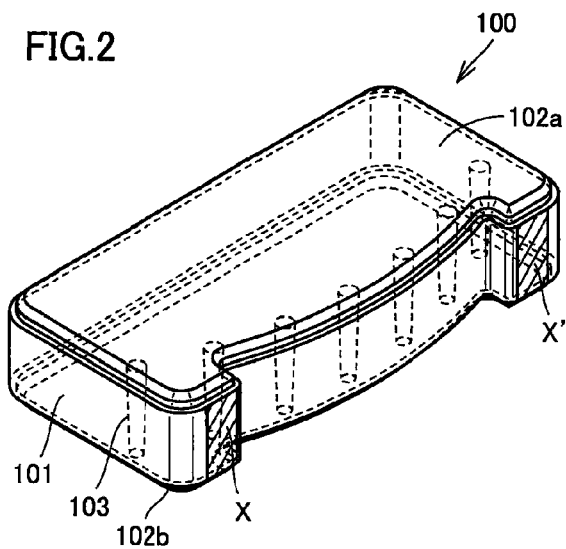
FIG. 2 is a schematic perspective view showing the microchip shown in FIG. 1.
Figure 3:
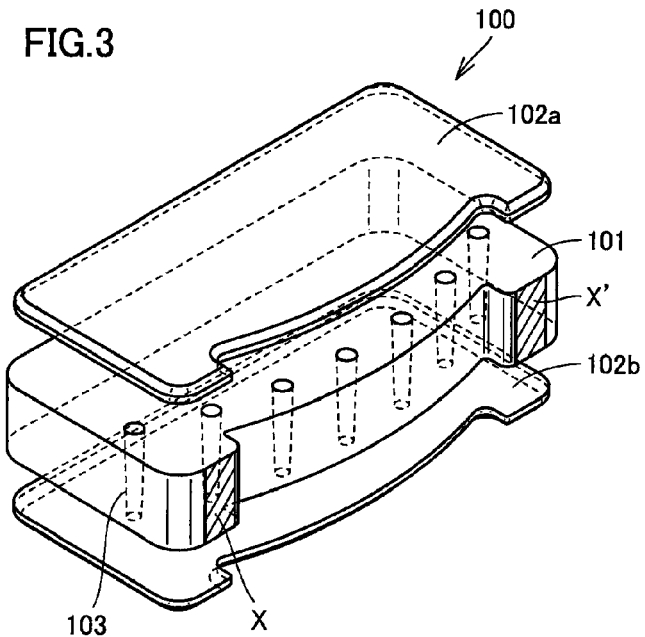
FIG. 3 is a schematic exploded perspective view showing the microchip shown in FIG. 1.

FIGS. 1 to 3 are schematic views showing one example of a microchip according to a first embodiment of the present invention, where FIG. 1 is a schematic top view, FIG. 2 is a schematic perspective view, and FIG. 3 is a schematic exploded perspective view. A microchip 100 shown in FIGS. 1 to 3 is configured by laminating a first substrate 101, and two second substrates 102a and 102b which are transparent substrates, in such manner that second substrates 102a and 102b sandwich first substrate 101. First substrate 101 is formed with a total of seven pass-through holes 103 passing in a thickness direction of the substrate, and substrate surfaces of two second substrates 102a and 102b seal an opening of pass-through hole 103. A diameter of the opening of pass-through hole 103 on second substrate 102b side is about 1 mm, and a diameter of the opening on second substrate 102a side is about 1.5 mm. Such opening diameters are not particularly limited. A space (cavity) configured by pass-through hole 103 and the surfaces of second substrates 102a and 102b is an optical measurement cuvette of the microchip. Examinations/analyses (e.g., detection of a specific component in a mixed liquid) of an examining/analyzing object (e.g., mixed liquid of specimen (such as blood) and liquid reagent) accommodated in the optical measurement cuvette are conducted by irradiating the optical measurement cuvette with a detection light, for example, from a lower side of the microchip (e.g., second substrate 102b side) in a direction substantially perpendicular to the surface of the microchip, and measuring transmittance and the like of the light exit from an upper side of the microchip (e.g., second substrate 102a side).

The specimen mixed with the liquid reagent may be the specimen itself or may be a specific component separated from the relevant specimen at inside or outside the microchip. The specimen encompasses both meanings in the present specification.

Although not particularly limited, for example, a measuring portion for measuring specimen or liquid reagent, a mixing portion for mixing the specimen and the liquid reagent, and other portions arranged as necessary, as well as, a fine fluid path (including fluid path for introducing liquid to the optical measurement cuvette) for appropriately connecting each portion are formed as portions configuring a fluid circuit in the interior of microchip 100 in addition to the optical measurement cuvette, but they are not described in FIGS. 1 to 3.

The microchip interiorly including portions such as the measuring portion and the mixing portion as well as the fluid path connecting such portions along with the optical measurement cuvette as portions configuring the fluid circuit is fabricated by laminating the second substrate on the first substrate with the groove formed on the substrate surface and the pass-through hole passing in the thickness direction of the substrate in such manner that a groove formed surface of the first substrate faces the second substrate. The fluid circuit consisting of a space (cavity) configured by the groove formed on the surface of the first substrate and the pass-through hole and a surface on the side facing the first substrate of the second substrate is thereby formed. Shapes and patterns of the groove formed on the surface of the first substrate are not particularly limited, and are determined such that a structure of the space configured by the groove and the surface of the second substrate becomes a desired appropriate fluid circuit structure.

In the microchip shown in FIGS. 1 to 3, a black substrate is used for first substrate 101, the size thereof being about 62 mm horizontally (A in FIG. 1)×about 30 mm vertically (B in FIG. 1)×about 9 mm in thickness. Two second substrates 102a and 102b that are transparent substrates have substrate surfaces smaller than the substrate surface of first substrate 101. Specifically, an outer shape of the substrate surfaces of second substrates 102a and 102b is approximately similar to first substrate 101, but has a size slightly reduced compared to first substrate 101 (see FIG. 1). Side wall surfaces of second substrates 102a and 102b are thus positioned on the inner side of the microchip than a side wall surface of first substrate 101 over the entire periphery of the microchip by laminating first substrate 101 and second substrates 102a and 102b at appropriate arrangement, and regions where the substrate surfaces of first substrate 101 (surface to be laminated with second substrates 102a and 102b) are partially exposed at a width of about 0.3 mm (C in FIG. 1) are formed when the microchip is seen from above and below. The thicknesses of second substrates 102a and 102b are both 1.6 mm. Materials of the first substrate and the second substrate are not particularly limited, and plastic substrate and the like can be used.

Thus, microchip 100 has a side wall surface region where the side wall surface of first substrate 101 having pass-through hole 103 mainly configuring the optical measurement cuvette is projected more than the side wall surfaces of laminated second substrates 102a and 102b. In the microchip shown in FIGS. 1 to 3, the projecting side wall surface region is formed over the entire outer periphery of the microchip.

The side wall surface projecting from the side wall surface of the second substrate (positioned on the outer side of the microchip) of the side wall surfaces of the first substrate is referred to as a "projecting side wall surface" of the first substrate. Therefore, according to the microchip in which the substrate formed with the portion (pass-through hole) mainly configuring the optical measurement cuvette includes the projecting side wall surface, an alignment precision of an optical axis of the detection light, which irradiates the optical measurement cuvette, and the optical measurement cuvette in the optical measurement can be enhanced by setting the projecting side wall surface of the first substrate as the surface (hereinafter also referred to as "alignment reference plane") to be pressed against a fixed surface in a microchip mounting portion of a centrifugal device. This aspect will be described in more detail below.

As described above, in the microchip interiorly including the fluid circuit such as the microchip of the present invention, a series of operations in the fluid circuit such as measuring of the specimen and the liquid reagent, mixing of the specimen and the liquid reagent, as well as, moving of the specimen, the liquid reagent, and the mixed liquid to each portion (e.g., introduction of the mixed liquid to the optical measurement cuvette) is performed by applying a centrifugal force in an appropriate direction with respect to the microchip. The application of the centrifugal force on the microchip is carried out, for example, using the centrifugal device including the microchip mounting portion for mounting the microchip.

Figure 4:
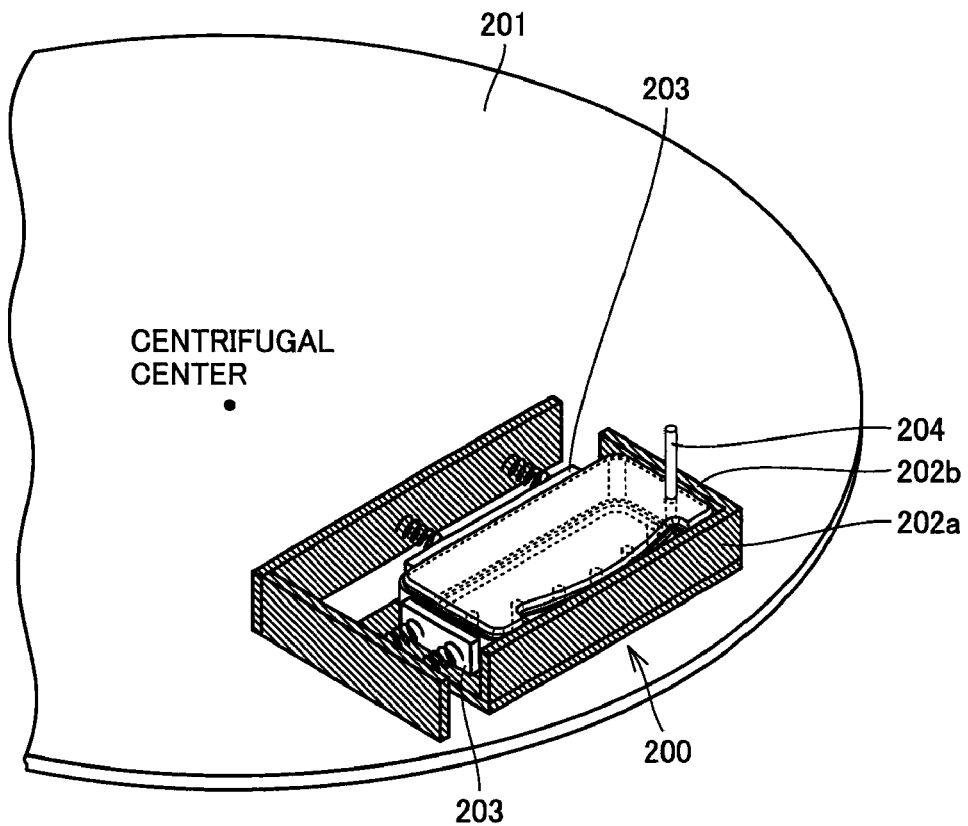
FIG. 4 is a schematic perspective view showing a state in which the microchip is mounted on a centrifugal device including a microchip mounting portion configured by a fixed wall for supporting the microchip.

The centrifugal device for applying the centrifugal force to the microchip may be configured including a first circular stage that freely rotates (rotation for revolving the microchip) with the centrifugal center as the axis, where the microchip mounting portion is arranged on a surface of the first circular stage or on a surface of a second circular stage for rotating the microchip arranged on the first circular stage. The configuration of the microchip mounting portion is not particularly limited, and may be a groove for fitting the microchip having substantially the same shape as the outer shape of the microchip or may be configured by a fixed wall for supporting the mounted microchip. FIG. 4 is a schematic perspective view showing a state in which the microchip shown in FIGS. 1 to 3 is mounted on the centrifugal device including the microchip mounting portion configured by the fixed wall for supporting the microchip. As shown in FIG. 4, a fixing tool 203 using a plate spring, a spring, and the like for fixing the position of the mounted microchip is added to a microchip mounting portion 200. The microchip mounted so as to lie along fixed walls 202a and 202b for supporting the microchip arranged on a first circular stage 201 of the centrifugal device is pressed by fixing tool 203, and the centrifugal force is applied on the microchip by rotating first circular stage 201 in such state. Although not shown in FIG. 4, a second circular stage that freely rotates for rotating the microchip is preferably arranged on first circular stage 201, and the microchip mounting portion including fixed walls 202a and 202b, and fixing tool 203 is installed on the second circular stage. The direction of the centrifugal force applied to the microchip can be easily adjusted by arranging the second circular stage.

After a predetermined centrifugal operation is performed, the optical measurement cuvette of the microchip is irradiated with a detection light 204 by an optical measurement device (not shown) positioned at the lower part of first circular stage 201, and the transmittance and the like of the light exit from the upper surface of the microchip are measured to conduct examinations/analyses (see FIG. 4). In the microchip shown in FIGS. 1 to 3 including a plurality of optical measurement cuvettes, different types of liquid can be accommodated in each optical measurement cuvette, so that a plurality of examinations/analyses can be conducted with one microchip. The irradiation with detection light 204 on each optical measurement cuvette can be carried out by rotating first circular stage 201, and arranging each optical measurement cuvette in order on the optical axis of detection light 204. The irradiation with the detection light may be carried out from the upper surface side of the microchip.

The microchip mounted on microchip mounting portion 200 as described above sometimes slightly move inside microchip mounting portion 200 due to the application of the centrifugal force in various directions even if this microchip is supported by fixing tool 203 and the like, whereby the position of the optical measurement cuvette and the optical axis of detection light 204 shifts in the optical measurement (in irradiation with detection light), and optical measurement becomes difficult. Therefore, in order to resolve such positional shift and arrange the opening of the pass-through hole configuring the optical measurement cuvette on the optical axis, it is vital that, at least, the direction of the centrifugal force applied the last on the microchip (i.e., centrifugal force applied immediately before the optical measurement) at least needs to be a direction one of the side wall surfaces of the microchip is pressed against fixed wall 202a and the like (see FIG. 4) to fine tune the position of the microchip in microchip mounting portion 200 along with the centrifugal operation, and to arrange and fix the microchip at an appropriate position in the optical measurement. Here, microchip mounting portion 200 is installed at a position where when the microchip is pressed against the fixed wall and a position of the microchip is adjusted, the opening of the pass-through hole configuring the optical measurement cuvette can be arranged on the optical axis by the rotation of first circular stage 201. If the microchip mounting portion consists of the groove for fitting the microchip, the fixed wall to which the side wall surface of the microchip is pressed against becomes an inner wall surface of the groove.

However, even if the side wall surface of the microchip can be pressed against the inner wall surface of the fixed wall of the microchip mounting portion by the last centrifugal operation, the alignment between the optical axis of the detection light and the optical measurement cuvette is sometimes difficult due to the following reasons in microchips not complying with the present invention. A microchip in which a side wall surface of a first substrate and a side wall surface of a second substrate are configured to form the same plane (i.e., microchip in which the first substrate does not include the projecting side wall surface) or a microchip in which a side wall surface of a second substrate is positioned on the outer side than a side wall surface of a first substrate (i.e., microchip in which the second substrate includes the projecting side wall surface) may have numerous manufacturing factors that may cause variation in the structure of the microchip side wall surface such as variation in dimensions of the first substrate and the second substrate when manufacturing such microchip, positional shift when laminating the first substrate and the second substrate, and the like. For instance, in the microchip in which the side wall surface of the first substrate and the side wall surface of the second substrate are configured to form the same plane, the side wall surface of the first substrate or the second substrate may project out due to a slight positional shift etc. when laminating the first substrate and the second substrate. Furthermore, in the microchip in which the side wall surface of the second substrate is positioned on the outer side than the side wall surface of the first substrate, the extent of projection may change for every microchip due to a slight positional shift etc. when laminating the first substrate and the second substrate.

Therefore, it is difficult to sufficiently control the projecting precision of the projecting side wall surface in such microchips, and thus the variation in the structure of the microchip side wall surface among the microchips tends to become large, and the relative position relationship between the optical measurement cuvette and the inner wall surface tends to easily vary, and as a result, the alignment between the optical measurement cuvette and the optical axis of the detection light becomes difficult even if the operation of pressing the side wall surface of the microchip against the inner wall surface of the fixed wall of the microchip mounting portion is performed by applying the centrifugal force. Furthermore, if lamination shift between the first substrate and the second substrate occurs, a coordinate of the optical measurement cuvette may shift, or the perpendicularity of the plane to which the light enters in the optical measurement cuvette and the optical axis may degrade.

On the other hand, according to the microchip of the present invention having the projecting side wall surface at the first substrate formed with the pass-through hole configuring the optical measurement cuvette, the alignment precision of the optical measurement cuvette and the optical axis mainly depends simply on the dimensional precision of the first substrate (positional precision of the pass-through hole in the first substrate etc.), and thus an accurate alignment of the optical measurement cuvette and the optical axis can be achieved regardless of the microscopic dimensional variation of the second substrate or the microscopic positional shift of the second substrate when laminating the substrates. Thus, in the present invention, the alignment precision of the optical measurement cuvette and the optical axis mainly depends on the dimensional precision of the first substrate because the major portion (pass-through hole) configuring the optical measurement cuvette is formed in the first substrate.

In microchip 100 shown in FIGS. 1 to 3, first substrate 101 includes the projecting side wall surface over the entire side wall surface thereof. Therefore, "alignment reference plane" to be pressed against the inner wall surface of the fixed wall of the microchip mounting portion may be any one of the side wall surfaces of the microchip. However, the projecting side wall surface at the side wall surface closest to the optical measurement cuvette is preferably set as the alignment reference plane considering the fact that the alignment precision of the optical measurement cuvette and the optical axis depends on the dimensional precision of the first substrate. In view of such aspect, in microchip 100, projecting side wall surfaces X and X' shown in FIGS. 2 and 3 or the projecting side wall surface at the side wall surface positioned on the side opposite thereto are preferably set as the alignment reference plane. Projecting side wall surfaces X and X' are on the same plane.

Figure 5:
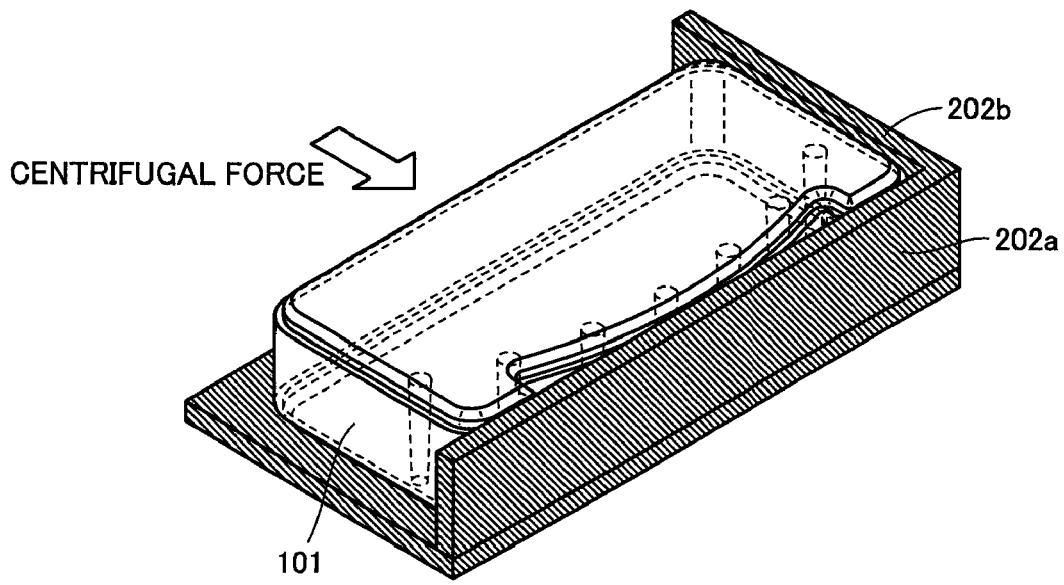
FIG. 5 is a schematic perspective view showing a state in which the microchip according to the first embodiment of the present invention is mounted on the microchip mounting portion of the centrifugal device, and a centrifugal force is applied to adjust a position of the microchip.

FIG. 5 is a schematic perspective view showing a state of mounting microchip 100 shown in FIGS. 1 to 3 on the microchip mounting portion of the centrifugal device, and applying the centrifugal force in the direction of the arrow to perform position adjustment of microchip 100. In FIG. 5, projecting side wall surfaces X and X' are the alignment reference planes. Projecting side wall surfaces X and X' are pressed against and closely attached to the inner wall surface of fixed wall 202a by the application of the centrifugal force in the direction of the arrow. Microchip 100 in the microchip mounting portion is thereby aligned, and the optical measurement cuvette and the optical axis of the detection light are coincided.

The projecting side wall surface of the first substrate set as the alignment reference plane preferably does not have projections on the surface. For instance, when fabricating the first substrate through injection molding, a gate position may be set in the side wall surface of the first substrate, whereby the projection may be formed on the side wall surface of the first substrate. Therefore, if the gate position is set in the side wall surface of the first substrate, the gate position is preferably provided at the side wall surface that is not the alignment reference plane. If the projection exists on the alignment reference plane, the relative position relationship of the optical measurement cuvette and the inner wall surface of the fixed wall varies depending on the extent of the projection, and the alignment of the optical measurement cuvette and the optical axis of the detection light consequently becomes difficult.

The projecting side wall surface of the first substrate set as the alignment reference plane is preferably a plane. Therefore, when aligning the microchip by pressing the alignment reference plane against the inner wall surface of the fixed wall by applying the centrifugal force, the precision of alignment can be enhanced since the alignment can be carried out at the plane. If the projecting side wall surface of the first substrate is a curved surface or a spot-like surface, an accurate alignment may not be carried out when the wall surface is pressed against the inner wall surface of the fixed wall.

The projecting side wall surface of the first substrate set as the alignment reference plane is preferably the side wall surface having the highest projecting degree (protruding the most) of the side wall surfaces of the microchip. The microchip mounting portion then can be relatively easily formed. In other words, the microchip mounting portion arranged in the centrifugal device may be the groove (holder) for fitting the microchip, but a structure that escapes the side wall surface protruded more than the projecting side wall surface (e.g., accommodates the protruded portion) needs to be formed in the groove (holder) of the microchip mounting portion so as not to inhibit the projecting side wall surface (alignment reference plane) from being pressed against the fixed wall of the groove when the microchip includes the side wall surface protruded more than the projecting side wall surface acting as the alignment reference plane. However, the structure of such microchip mounting portion is sometimes difficult to form by injection molding or drill molding.

According to the microchip shown in FIGS. 1 to 3 having the projecting side wall surface on the first substrate, the formation of the microchip mounting portion is facilitated due to the reasons similar to the above. That is, when the second substrate includes the projecting side wall surface, and the side wall surface of the first substrate is set as the alignment reference plane, a structure of escaping the projecting portion of the second substrate needs to be formed in the microchip mounting portion, but such structure is sometimes difficult to form.

The microchip shown in FIGS. 1 to 3 may be subjected to various modifications within a scope not deviating from the purpose of the present invention. First, the numerical values related to the dimension of the microchip are one example, and are not limited to the above numerical values.

In the microchip shown in FIGS. 1 to 3, the projecting width (C in FIG. 1) with respect to the second substrate of the side wall surface of first substrate 101 is about 0.3 mm, but is not limited thereto, and may be smaller than or equal to about 1 mm when the vertical and horizontal lengths of the first substrate take the above values. The projecting width does not need to be even over the entire outer periphery of the microchip, and the projecting width with respect to second substrate 102a and the projecting width with respect to second substrate 102b may be the same or may be different.

In the microchip shown in FIGS. 1 to 3, the projecting side wall surface is formed over the entire outer periphery of the microchip, but is not limited thereto, and the projecting side wall surface merely needs to be formed at least in the region set for the alignment reference plane. Considering the easiness to control the dimensional precision when manufacturing the substrate and to control the positional precision in lamination when laminating the substrates, a method of fabricating the second substrate of substantially similar figure to the outer shape of the first substrate surface and having a slightly reduced size, and laminating second substrate to the first substrate to fabricate the microchip in which the projecting side wall surface is formed over the entire outer periphery is preferable.

In the microchip shown in FIGS. 1 to 3, seven pass-through holes 103 configuring the optical measurement cuvette are formed in the first substrate, but not limited thereto, and the optical measurement cuvette merely needs to be one or more. The first substrate does not necessarily need to be a black substrate and may be a transparent substrate or substrate of other colors. When adhering the first substrate and the second substrate by fusion of the substrate surface by light irradiation and having the second substrate as the transparent substrate, the first substrate is preferably a colored substrate, and more preferably a black substrate. The blackening is performed by adding black pigment such as carbon black and the like to resin that is the substrate material. The second substrate does not necessarily need to be entirely transparent, but the region sealing the opening of the pass-through hole of the first substrate at least needs to be transparent to enable optical measurement.

Figure 6:
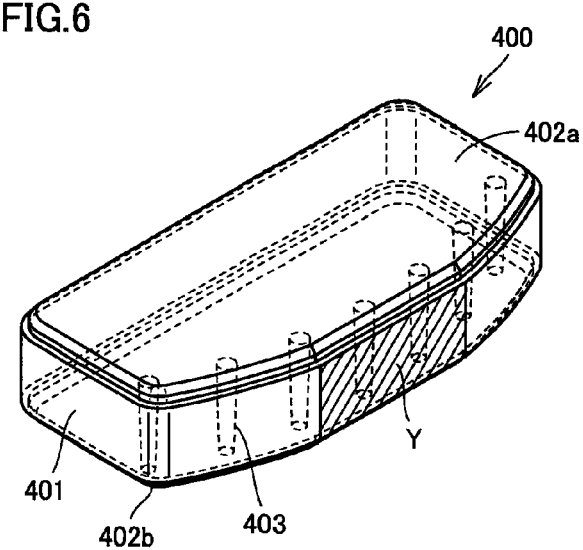
FIG. 6 is a schematic perspective view showing another example of the microchip according to the first embodiment of the present invention.

Furthermore, the outer shape of the microchip is not limited to the shape shown in FIGS. 1 to 3, and may take various shapes. FIG. 6 is a schematic perspective view showing another example of the microchip according to the first embodiment of the present invention. Similar to the microchip of FIGS. 1 to 3, a microchip 400 shown in FIG. 6 is formed by laminating a first substrate 401 and two second substrates 402a and 402b that are transparent substrates, in such manner that second substrates 402a and 402b sandwich first substrate 401, where the projecting side wall surface of the first substrate is formed over the entire outer periphery of the microchip. First substrate 401 includes a total of seven pass-through holes 403 configuring the optical measurement cuvette. In microchip 400 shown in FIG. 6, a projecting side surface Y or a projecting side wall surface at the side wall surface positioned on the side facing thereto is set as an alignment reference plane.

Figure 7:
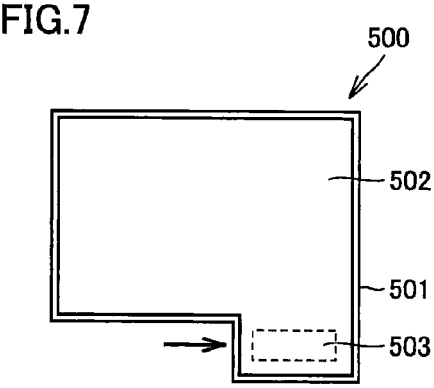
FIG. 7 is a schematic top view showing another further example of the microchip according to the first embodiment of the present invention.
Figure 8:
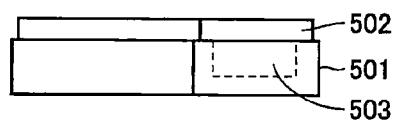
FIG. 8 is a schematic side view showing the microchip shown in FIG. 7.
Figure 9:
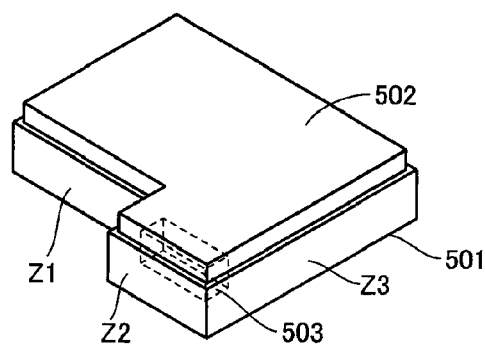
FIG. 9 is a schematic perspective view showing the microchip shown in FIG. 7.

FIGS. 7 to 9 are schematic views showing another further example of the microchip according to the first embodiment of the present invention, where FIG. 7 is a schematic top view, FIG. 8 is a schematic side view, and FIG. 9 is a schematic perspective view. A microchip 500 shown in FIGS. 7 to 9 is formed by laminating a first substrate 501 that is a transparent substrate, and a second substrate 502 that is a black substrate, in such manner that an opening of a groove 503 formed at the surface of first substrate 501 is sealed by the substrate surface of second substrate 502. A space (cavity) configured by groove 503 and the second substrate surface becomes the optical measurement cuvette of the microchip. The optical measurement cuvette is irradiated with the detection light at an angle substantially parallel to the surface of the microchip in microchip 500 shown in FIGS. 7 to 9. In FIGS. 7 to 9, other portions and fluid paths of the fluid circuit are not described, similar to the case of FIGS. 1 to 3.

In microchip 500 shown in FIGS. 7 to 9, second substrate 502 has a substrate surface smaller than the substrate surface of first substrate 501. Specifically, the outer shape of second substrate 502 is approximately the same as first substrate 501, but has a size slightly reduced from first substrate 501 (see FIG. 7). The projecting side wall surface is formed at the first substrate that is a substrate formed with a portion (groove) mainly configuring the optical measurement cuvette over the entire outer periphery of the microchip by laminating first substrate 501 and second substrate 502. According to such configuration, effects similar to the microchip shown in FIGS. 1 to 3 are obtained.

In microchip 500 shown in FIGS. 7 to 9, the alignment reference plane can be set to any projecting side wall surface. With reference to FIG. 9, for example, a projecting side wall surface Z1, Z2, or Z3 may be set as the alignment reference plane, or other projecting side wall surface may be set as the alignment reference plane. However, the projecting side wall surface at the side wall surface closest to the optical measurement cuvette is preferably set as the alignment reference plane considering the fact that the alignment precision of the optical measurement cuvette and the optical axis depends on the dimensional precision of the first substrate. Furthermore, projecting side wall surface Z2 or Z3 is preferably set as the alignment reference plane considering parallelism of the optical measurement cuvette and the optical axis, and perpendicularity of the light incident end face of the optical measurement cuvette and the optical axis. The projecting side wall surface of the first substrate set as the alignment reference plane preferably does not include projections and is more preferably a plane. Microchip 500 shown in FIGS. 7 to 9 may be subjected to modifications similar to the microchip shown in FIGS. 1 to 3.

Second Embodiment

Figure 10A:
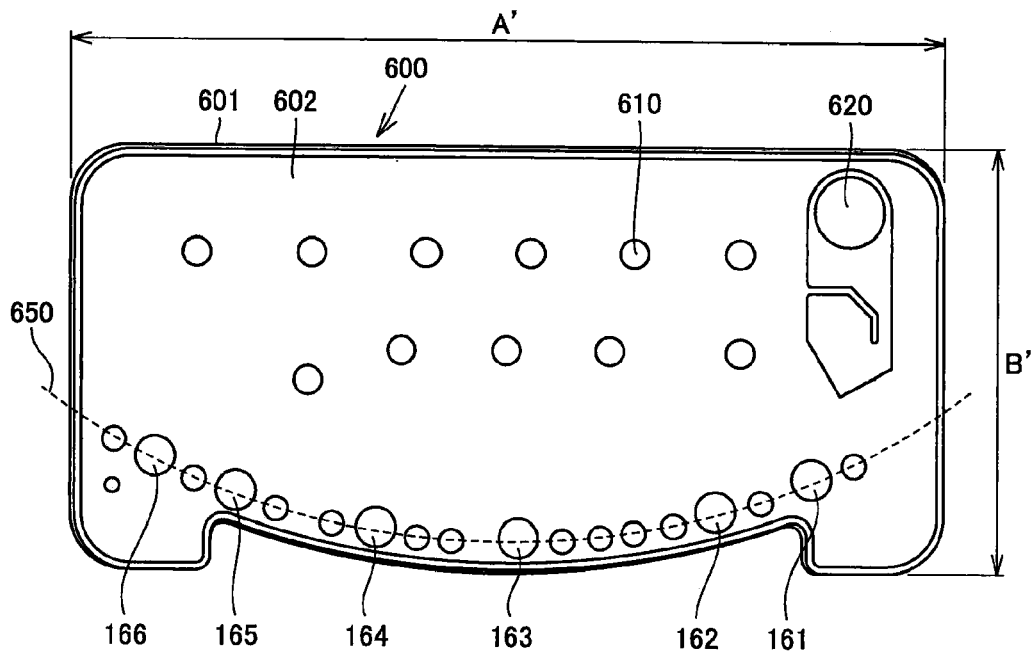
FIGS. 10A, 10B, and 10C are schematic views showing one example of a microchip according to a second embodiment of the present invention.
Figure 10B:
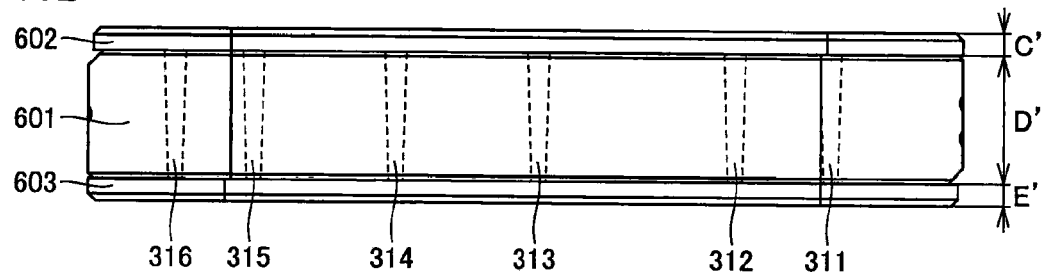
Figure 10C:
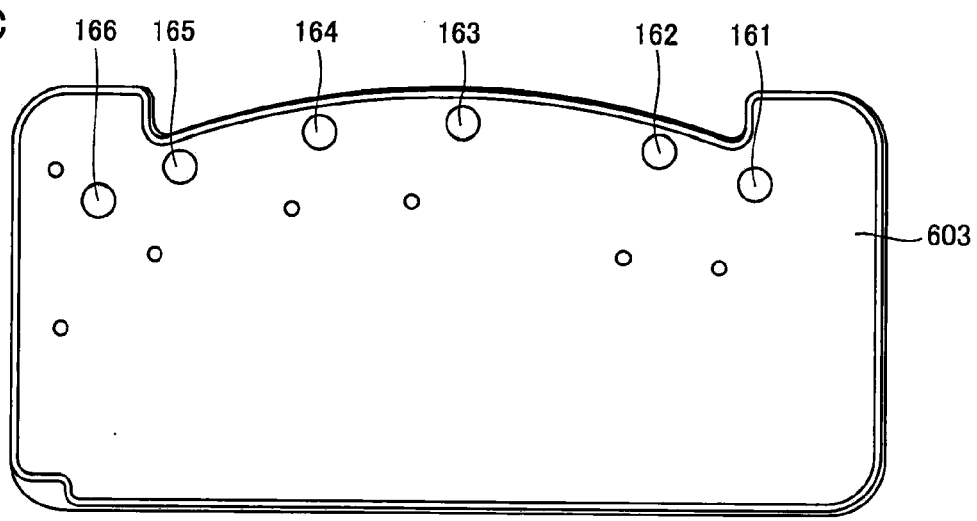

A microchip according to a second embodiment of the present invention will now be described. FIGS. 10A to 10C are schematic views showing one example of the microchip according to the second embodiment of the present invention, where FIG. 10A is a schematic top view, FIG. 10B is a schematic side view, and FIG. 10C is a schematic bottom view. A microchip 600 shown in FIGS. 10A to 10C is formed by laminating two second substrates 602, 603 that are transparent substrates, on both sides of a first substrate 601 that is a black substrate (see FIG. 10B). Vertical and horizontal lengths of the substrates are not particularly limited, and may be about 62 mm horizontally (A' in FIG. 10A)×about 30 mm vertically (B' in FIG. 10A). Thicknesses of second substrate 602, first substrate 601, and second substrate 603 (C', D', and E' in FIG. 10B) may be, for example about 1.6 mm, about 9 mm, and about 1.6 mm, respectively. The vertical and horizontal lengths and the thickness of the substrate are not limited thereto.

Liquid reagent introducing ports 610 (total of eleven) passing in a thickness direction and a specimen introducing port 620 for introducing a specimen (e.g., whole blood) into the fluid circuit of the microchip are formed in second substrate 602. The liquid reagent is a reagent for mixing or reacting with the specimen, or for processing the specimen, and is in the liquid reagent holding portion of the fluid circuit in advance before the actual use (examinations, analyses and the like of specimen) of the microchip. The microchip is normally provided for actual use with liquid reagent introducing port 610 sealed with a sealing label and the like after injecting the liquid reagent from liquid reagent introducing port 610.

First substrate 601 is formed with a groove on both sides and a pass-through hole passing in the thickness direction of the substrate, and a fluid circuit of two layers is formed inside the microchip by laminating second substrates 602, 603 on both sides of first substrate 601. The fluid circuit consists of a space (cavity) configured by the groove formed on the first substrate surface and the pass-through hole and the surface on the side facing the first substrate of the second substrate. Here, two layers mean that two fluid circuits are arranged at different positions with respect to the thickness direction of the microchip. The two fluid circuits are communicated by one or a plurality of pass-through holes formed in first substrate 601.

Of the plurality of pass-through holes formed in first substrate 601, pass-through holes 311, 312, 313, 314, 315, and 316 (total of six) shown in FIG. 10B configure optical measurement cuvettes 161, 162, 163, 164, 165, and 166 with the substrate surfaces of second substrates 602 and 603 which seal the openings of the pass-through holes. In other words, the optical measurement cuvette consists of a space configured by pass-through holes 311, 312, 313, 314, 315, and 316 (total of six) and the substrate surfaces of second substrates 602 and 603 which seal the openings of the pass-through holes. A diameter of an opening of pass-through holes 311 to 316 on second substrate 602 side can be, for example, about 1.5 mm, and a diameter of the opening on second substrate 603 side can be, for example, about 1 mm, but are not particularly limited.

The examinations/analyses (e.g., detection of a specific component in the mixed liquid) of the examining/analyzing object (e.g., mixed liquid etc. of specimen and liquid reagent) accommodated in the optical measurement cuvette are conducted by irradiating the optical measurement cuvette with the detection light, for example, from the lower side (or upper side) of the microchip in a direction substantially perpendicular to the surface of the microchip, and measuring transmittance and the like of the light exit from the upper side (or lower side) of the microchip. As described above, the specimen mixed with the liquid reagent may be the specimen itself or may be a specific component separated from the specimen at inside or outside the microchip.

Microchip 600 shown in FIGS. 10A to 10C has a feature in that pass-through holes 311 to 316 configuring the optical measurement cuvette are arranged on a circumference 650 of the same circle at the surface of first substrate 601 (see FIG. 10A). According to such configuration, examinations/analyses of each examining/analyzing object introduced into the six optical measurement cuvettes can be easily and rapidly conducted.

In microchip 600 shown in FIGS. 10A to 10C, a series of operations in the fluid circuit such as measuring of the specimen and the liquid reagent, mixing of the specimen and the liquid reagent, as well as, moving of the specimen, the liquid reagent, and the mixed liquid to each portion is performed by applying a centrifugal force in an appropriate direction with respect to the microchip, as described above. The application of the centrifugal force on the microchip is carried out, for example, using the centrifugal device including the microchip mounting portion for mounting the microchip. The application of the centrifugal force on the microchip using the centrifugal device, the configuration of the centrifugal device and the optical measurement after a predetermined centrifugal operation are as described in the first embodiment.

With reference to FIG. 4, after the predetermined centrifugal operation is performed, the optical measurement cuvette of the microchip is irradiated with detection light 204 from a light source (not shown) positioned at the lower part of first circular stage 201, and the transmittance and the like of the light exit from the upper surface of the microchip are measured to conduct examinations/analyses on the examining/analyzing object in the optical measurement cuvette. In this case, in microchip 600 shown in FIGS. 10A to 10C including plurality of optical measurement cuvettes, although each optical measurement cuvette needs to be irradiated with the detection light, since the optical measurement cuvettes are arranged on the circumference of the same circle in microchip 600, the examinations/analyses can be easily and rapidly conducted by irradiating detection light 204 from the fixed light source, and arranging each optical measurement cuvette in order on the optical axis of detection light 204 by rotating first circular stage 201. The detection light may be irradiated from the upper surface side of the microchip.

The circle in "the same circle" is preferably a circle having the centrifugal center for applying the centrifugal force to the microchip as the center. More specifically, since the microchip is generally mounted on the first circular stage of the centrifugal device including the rotatable first circular stage and applied with the centrifugal force, the circle having the centrifugal center for applying the centrifugal force to the microchip as the center can also be referred to as a circle having the center of rotation of the first circular stage as the center.

The configuration of the fluid circuit of microchip 600 shown in FIGS. 10A to 10C will be more specifically described below.

Figure 11A:
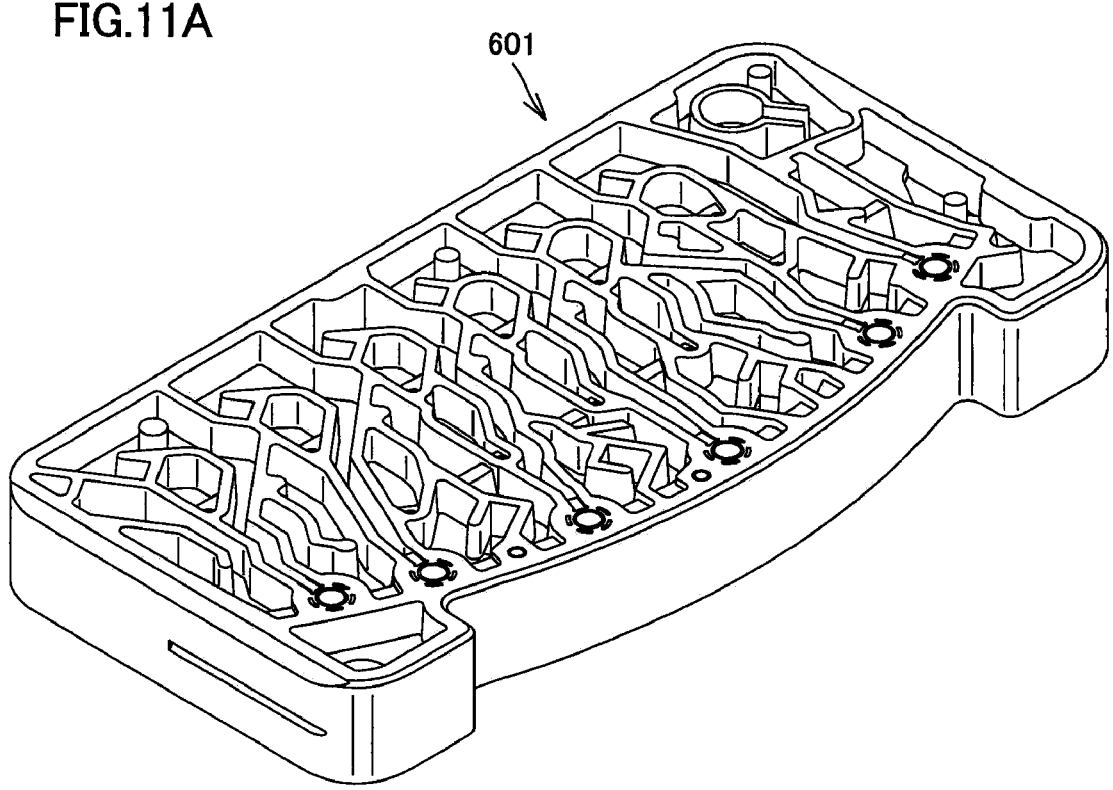
FIGS. 11A and 11B are perspective views showing a groove formed at the surface of the first substrate and a pass-through hole passing in the thickness direction of the substrate used in the microchip shown in FIGS. 10A to 10C.
Figure 11B:
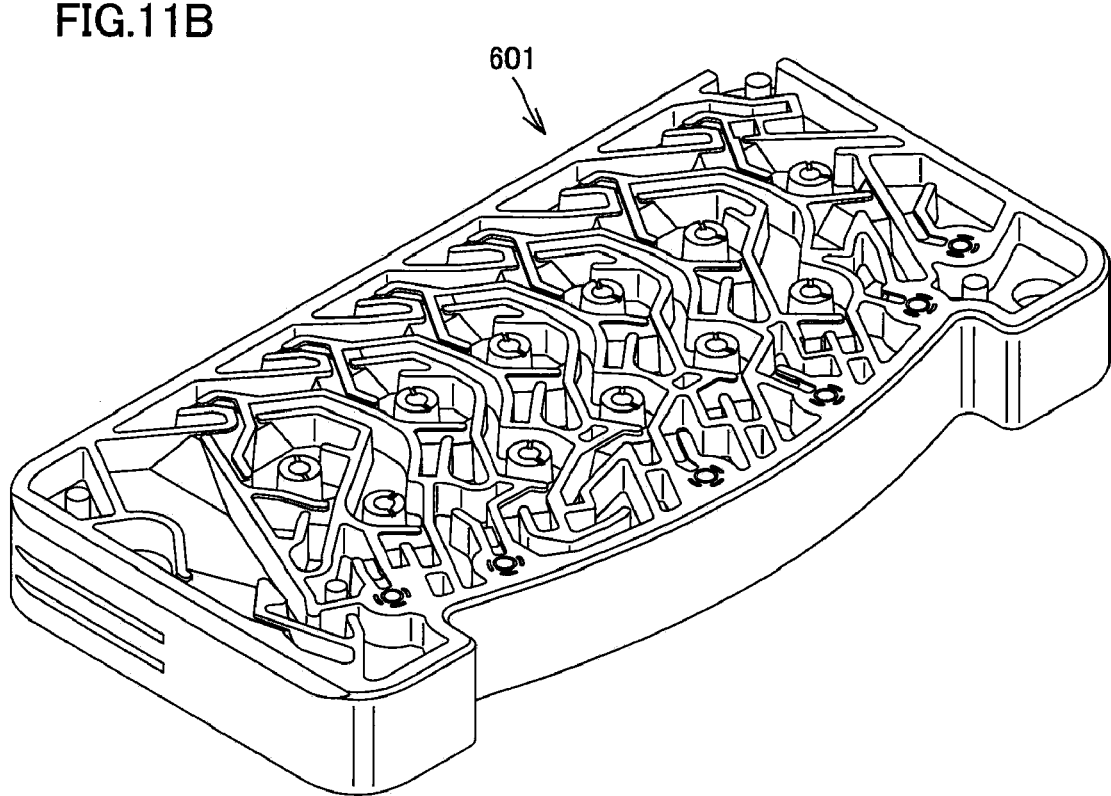

FIGS. 11A and 11B are perspective views showing a groove formed on a surface of first substrate 601 and a pass-through hole passing in the thickness direction of the substrate, where FIG. 11A is a perspective view showing the groove formed on the surface on second substrate 602 side (hereinafter simply referred to as "upper side") and the pass-through hole passing in the thickness direction of the substrate, and FIG. 11B is a perspective view showing the groove formed on the surface on second substrate 603 side (hereinafter simply referred to as "lower side") and the pass-through hole passing in the thickness direction of the substrate. As shown in FIGS. 11A and 11B, first substrate 601 is formed with an appropriately designed groove on both surfaces and the plurality of pass-through holes passing through the substrate in the thickness direction. Such grooves and pass-through holes configure the fluid circuit of two layers including each portion where the fluid processing of the specimen, the liquid reagent, and the mixed liquid thereof is performed and fine fluid paths appropriately connecting the portions, along with the surface on first substrate 601 side of second substrates 602 and 603.

Figure 12:
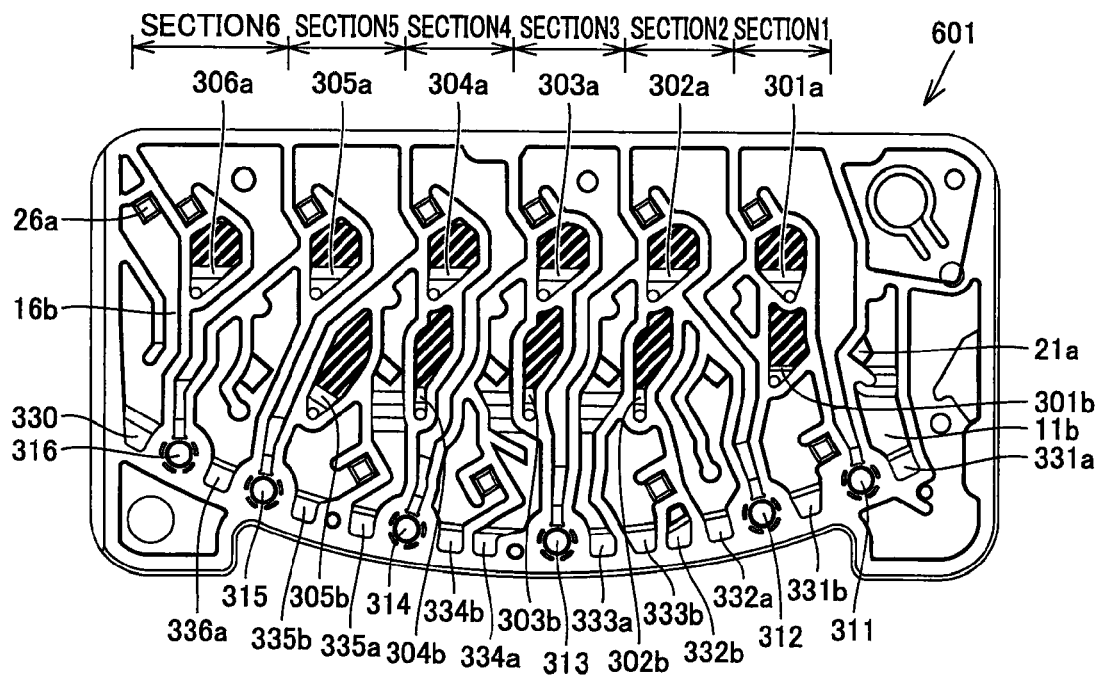
FIG. 12 is a top view showing the first substrate used in the microchip shown in FIGS. 10A to 10C.
Figure 13:
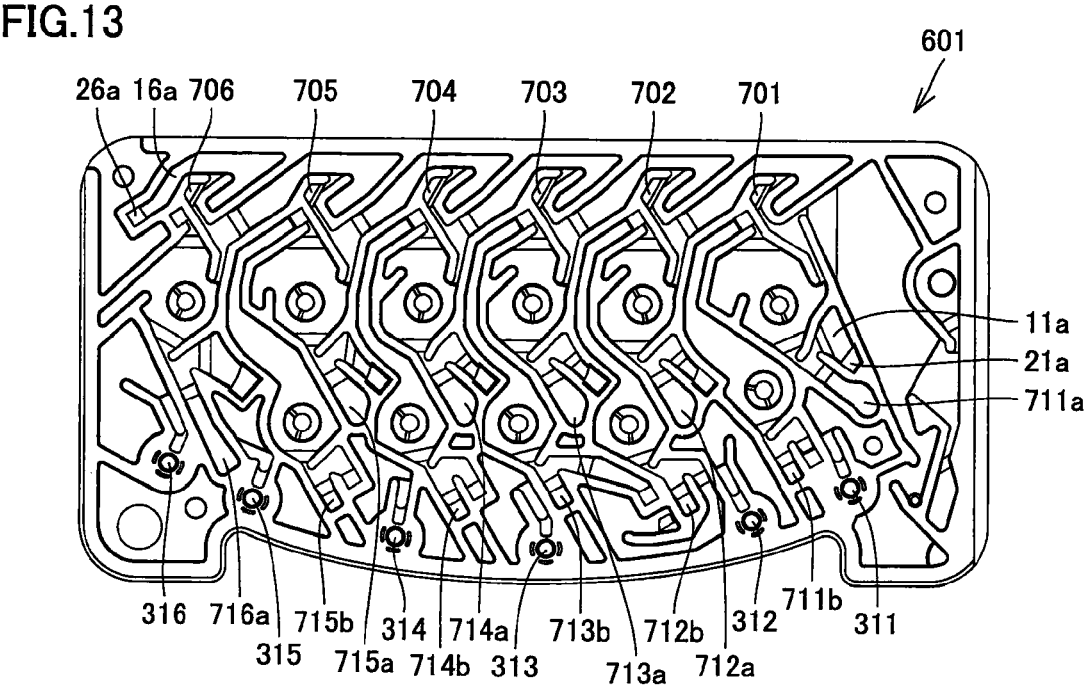
FIG. 13 is a bottom view showing the first substrate used in the microchip shown in FIGS. 10A to 10C.

FIGS. 12 and 13 respectively show a top view and a bottom view of first substrate 601. That is, FIG. 12 shows a fluid circuit on the upper side of the fluid circuit of two layers of microchip 600, and FIG. 13 shows a fluid circuit on the lower side. In FIG. 13, the fluid circuit on the lower side is shown with the left and the right inverted so that a correspondence relationship with the fluid circuit on the upper side shown in FIG. 12 can be clearly understood. Microchip 600 is a multi-item chip capable of conducting examinations/analyses on six items with one specimen, where the fluid circuit thereof is divided into six sections (sections 1 to 6 in FIG. 12) so that examinations/analyses of six items can be conducted (the sections are connected to each other in a specimen measuring portion installing region (upper region of lower side fluid circuit)). Each section is arranged with one or two liquid reagent holding portions holding the liquid reagent (total of eleven liquid reagent holding portions 301a, 301b, 302a, 302b, 303a, 303b, 304a, 304b, 305a, 305b, and 306a in FIG. 12). The specimen introduced from specimen introducing port 620 in FIG. 10A is separated and removed with blood cell component, and then distributed to each section and measured, and then mixed with the separately measured one type or two types of liquid reagent in each section, and introduced to pass-through holes 311, 312, 313, 314, 315, and 316 configuring the optical measurement cuvette. The mixed liquid introduced to each optical measurement cuvette is provided for optical measurement of irradiating the optical measurement cuvette with the light from a direction substantially perpendicular to the surface of the microchip etc., and measuring the transmitted light thereof, and detection and the like of a specific component in the mixed liquid are carried out. A series of processing is performed by moving the liquid reagent, the specimen, or the mixed liquid in an appropriate order to each portion of the fluid circuit of two layers arranged in each section by applying the centrifugal force in the appropriate direction with respect to the microchip.

In each section, specimen measuring portions for measuring the specimen (total of six of 701, 702, 703, 704, 705, 706 in FIG. 13) and liquid reagent measuring portions for measuring the liquid reagent (total of eleven liquid reagent measuring portions 711a, 711b, 712a, 712b, 713a, 713b, 714a, 714b, 715a, 715b, and 716a in FIG. 13) are arranged in the lower side fluid circuit. Each specimen measuring portion is connected in series by the flow path.

As shown in FIG. 12, microchip 600 is arranged with an overflow specimen accommodating portion 330 for accommodating the specimen overflowed from the specimen measuring portion in time of measurement, and overflow reagent accommodating portions 331a, 331b, 332a, 332b, 333a, 333b, 334a, 334b, 335a, 335b, and 336a for accommodating the liquid reagent overflowed from the liquid reagent measuring portion in time of measurement. Overflow specimen accommodating portion 330 is connected to specimen measuring portion 706 by way of a flow path 16a (see FIG. 13), a pass-through hole 26a passing in the thickness direction, and a flow path 16b (see FIG. 12). Each overflow reagent accommodating portion is connected to the corresponding liquid reagent measuring portion by way of a flow path and a pass-through hole. For instance, in section 17 liquid reagent measuring portion 711a for measuring the liquid reagent accommodated in liquid reagent holding portion 301a and overflow reagent accommodating portion 331a for accommodating the overflowed liquid reagent are connected by way of a flow path 11a (see FIG. 13), a pass-through hole 21a passing in the thickness direction, and a flow path 11b (see FIG. 12). Other overflow reagent accommodating portions are also the same.

Therefore, as the microchip includes the overflow specimen accommodating portion and the overflow reagent accommodating portions (hereinafter collectively referred to as overflow liquid accommodating portion), it can be easily checked whether the specimen or the liquid reagent is surely transferred to the specimen measuring portion or the liquid reagent measuring portion by the centrifugal operation, and the specimen measuring portion or the liquid reagent measuring portion is filled with specimen or liquid reagent by detecting the presence of the overflowed liquid in the overflow liquid accommodating portion. In other words, if the presence of the overflow liquid is detected in the overflow liquid accommodating portion, the specimen or the liquid reagent is guaranteed as accurately measured in the specimen measuring portion or the liquid reagent measuring portion. Thus, the reliability of examinations/analyses on the specimen can be enhanced, and determination on not to use the obtained examination/analysis data may be made if measurement abnormality is found. The measurement abnormality includes cases where the specimen or the liquid reagent is not introduced to the specimen measuring portion or the liquid reagent measuring portion due to malfunctioning of the centrifugal device; the specimen or the liquid reagent of an amount to be measured is not measured due to evaporation of the liquid reagent, deficiency in the specimen introducing amount by mistaken use of the user, laminating defects of the substrates in microchip manufacturing, and the like.

A method of detecting whether or not the overflowed specimen or the liquid reagent is present in the overflow liquid accommodating portion is not particularly limited, but a method of irradiating the overflow liquid accommodating portion with light from second substrate 602 side that is a transparent substrate, and measuring the intensity of the reflected light is preferably used. The light used is not particularly limited, and may be a single color light (e.g., laser light) having a wavelength of about 400 to 1000 nm, or a mixed light such as white light. The measurement of the intensity of the reflected light may be performed using a commercially available reflection sensor and the like.

In the method of detecting the presence of the overflowed liquid in the overflow liquid accommodating portion by measuring the intensity of the reflected light, basically, a ratio between a reflected light intensity obtained by irradiating the overflow liquid accommodating portion with the light from second substrate 602 side before the overflowed liquid is introduced into the overflow liquid accommodating portion, and a reflected light intensity obtained by irradiating the overflow liquid accommodating portion with the light from second substrate 602 side after the specimen or the liquid reagent is introduced into the specimen measuring portion or the liquid reagent measuring portion is obtained, and the presence of the overflow liquid is detected from the intensity ratio. In other words, determination is made that the overflowed liquid is present in the overflow liquid accommodating portion when the ratio (reflected light intensity after introduction/reflected light intensity before introduction) is smaller than one (reflected light intensity after introduction is smaller). However, if the manufacturing fluctuation among the microchips is small, and the reflected light intensity before introduction of the overflowed liquid is substantially constant among the microchips, the measurement of the reflected light intensity before introduction of the overflowed liquid may not be performed.

A method of detecting whether or not the liquid is present by measuring the reflected light intensity is not limited to the overflow liquid accommodating portion, and may be applied to other portions in the fluid circuit of the microchip. For instance, whether or not the liquid reagent is present in the liquid reagent holding portion can be checked by irradiating the liquid reagent holding portion with the light before the actual use of the microchip, and measuring the intensity of the reflected light. Thus, an abnormality that the liquid reagent is not sufficiently accommodated in the liquid reagent holding portion due to flow-out, evaporation and the like of the liquid reagent due to impact and the like when transporting the microchip holding the liquid reagent can be detected. Furthermore, whether or not the specimen, the liquid reagent, or the mixed liquid is surely present in the measuring portion the mixing portion can be checked by irradiating the specimen measuring portion, the liquid reagent measuring portion, the mixing portion where the specimen and the liquid reagent are mixed with light, and measuring the intensity of the reflected light. Thus, it can be guaranteed that the predetermined processing is surely performed by the application of the centrifugal force.

Microchip 600 includes a total of eleven overflow reagent accommodating portions corresponding to each liquid reagent and one overflow specimen accommodating portion, as described above, which are all preferably formed in the fluid circuit (upper side fluid circuit) on second substrate 602 side (see FIG. 12). In measuring the intensity of the reflected light, the microchip does not need to be turned over, and the presence of the overflowed liquid in all the overflow liquid accommodating portions can be easily and rapidly detected by forming all the overflow liquid accommodating portions in one fluid circuit. Furthermore, all the overflow liquid accommodating portions are preferably formed in one fluid circuit, and arranged on the circumference of the same circle at the surface of first substrate 601. All such overflow liquid accommodating portions are more preferably arranged on the circumference arranged with pass-through holes 311 to 316 configuring the optical measurement cuvette (see FIG. 12). The optical measurement cuvette and the overflow liquid accommodating portion are arranged on the circumference of the same circle at the surface of first substrate 601 so that the examinations/analyses, and the detection on the presence of the overflowed liquid can be easily and rapidly conducted by irradiating the detection light from a fixed transmitted light measurement light source and a fixed reflected light measurement light source (which maybe the same light source) and arranging each optical measurement cuvette and each overflow liquid accommodating portion on the optical axis of the detection light in order by rotating the first circular stage.

The fluid circuit structure of microchip 600 described above can be suitably applied as a fluid circuit structure of microchip 100 according to the first embodiment.

With reference to FIGS. 14A, 14B, 15A, 15B, 16A, 16B, 17A, 17B, 18A, 18B, 19A, 19B, 20A, and 20B, one example of fluid processing using microchip 600 will be described. The figures are views showing the state of liquid (specimen, liquid reagent, and mixed liquid) in the upper side fluid circuit (fluid circuit formed by first substrate 601 and second substrate 602), and the state of liquid in the lower side fluid circuit (fluid circuit formed by first substrate 601 and second substrate 603) in each step of the fluid processing. FIGS. 14A, 15A, 16A, 17A, 18A, 19A, and 20A are views showing the state of the liquid in the upper side fluid circuit, and FIGS. 14B, 15B, 16B, 17B, 18B, 19B, and 20B are views showing the state of the liquid in the lower side fluid circuit. In FIGS. 14B, 15B, 16B, 17B, 18B, 19B, and 20B, the lower side fluid circuit is shown with the left and the right inverted so that the correspondence relationship with the upper side fluid circuit shown in FIGS. 14A, 15A, 16A, 17A, 18A, 19A, and 20A can be clearly understood, similar to FIG. 13. In the following description, only the fluid processing in the fluid circuit of section 1 will be mainly described, but similar processing are performed in other sections, which can be clearly recognized by referencing the figures. A case where the specimen is the whole blood (blood plasma separated from the whole blood is sometimes referred to as specimen below) will be described below by way of example, but the type of specimen is not limited thereto.

(1) Blood Plasma Separation, Liquid Reagent Measuring Step

Figure 14A:
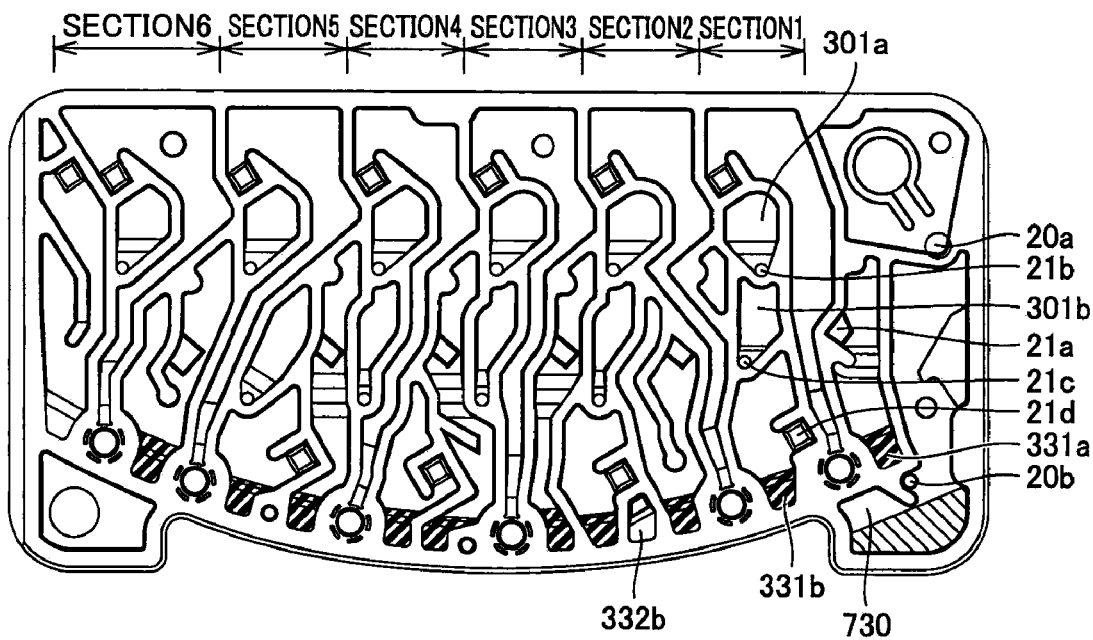
FIGS. 14A and 14B are views showing a state of liquid in an upper side fluid circuit and a state of liquid in a lower side fluid circuit in a blood plasma separation and liquid reagent measuring step.
Figure 14B:
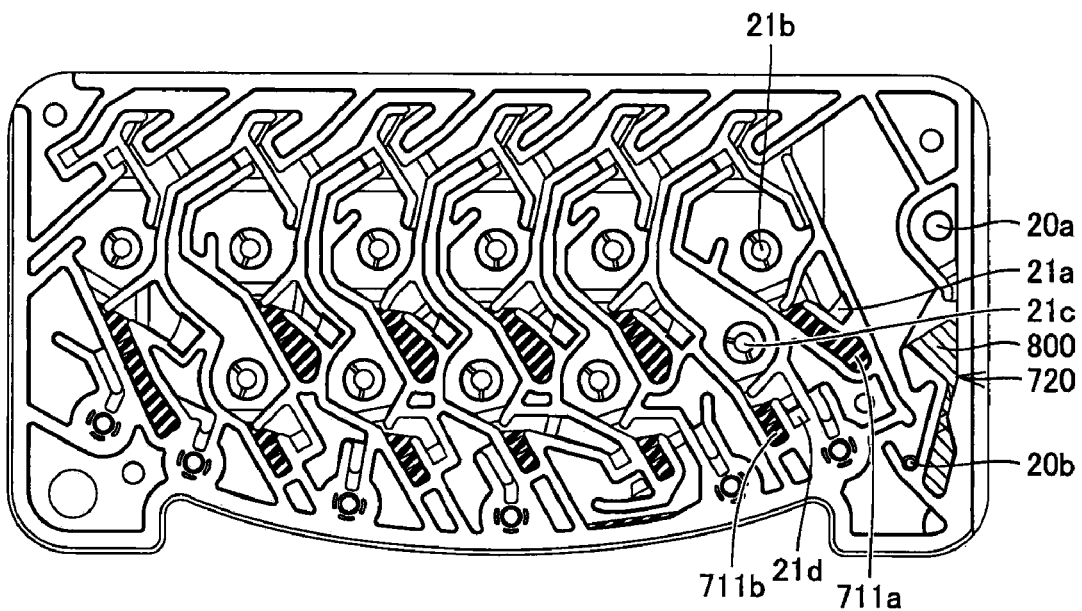
Figure 15A:
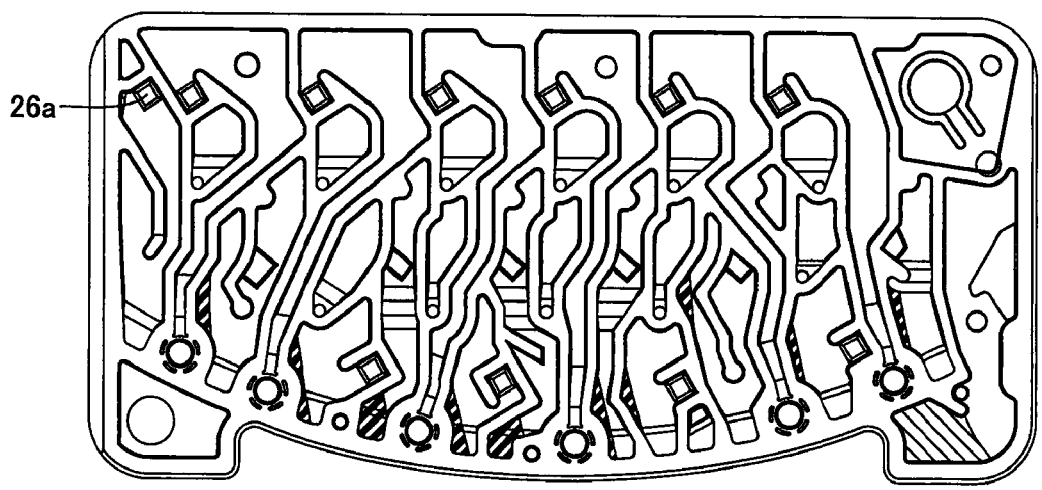
FIGS. 15A and 15B are views showing a state of liquid in the upper side fluid circuit and a state of liquid in a lower side fluid circuit in a specimen measuring step.
Figure 15B:
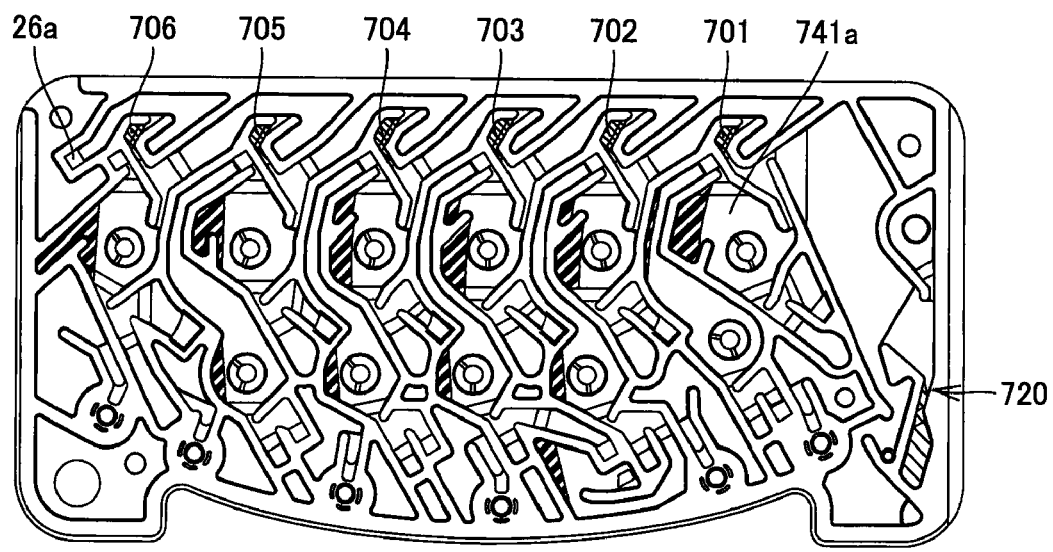
Figure 16A:
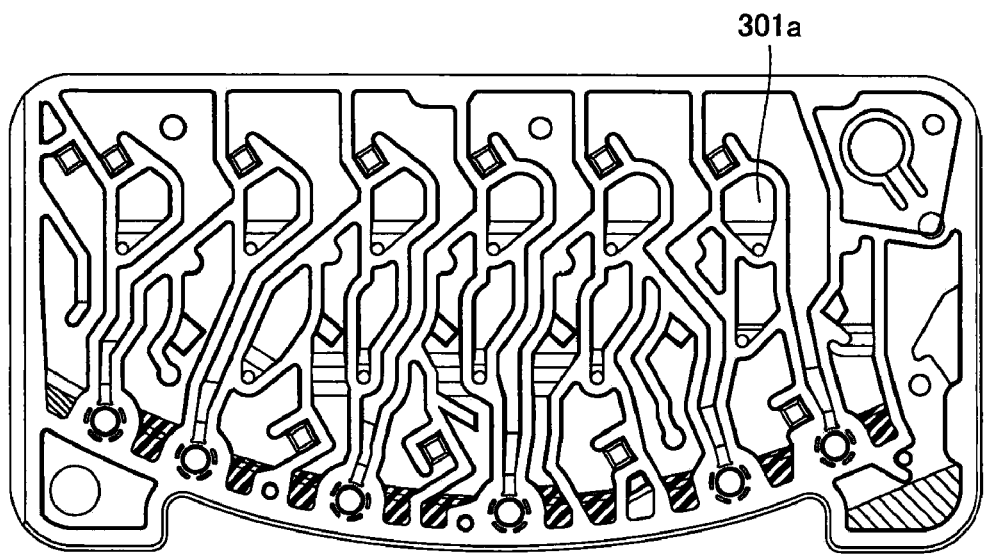
FIGS. 16A and 16B are views showing a state of liquid in an upper side fluid circuit and a state of liquid in a lower side fluid circuit in a first step of a first mixing step.
Figure 16B:
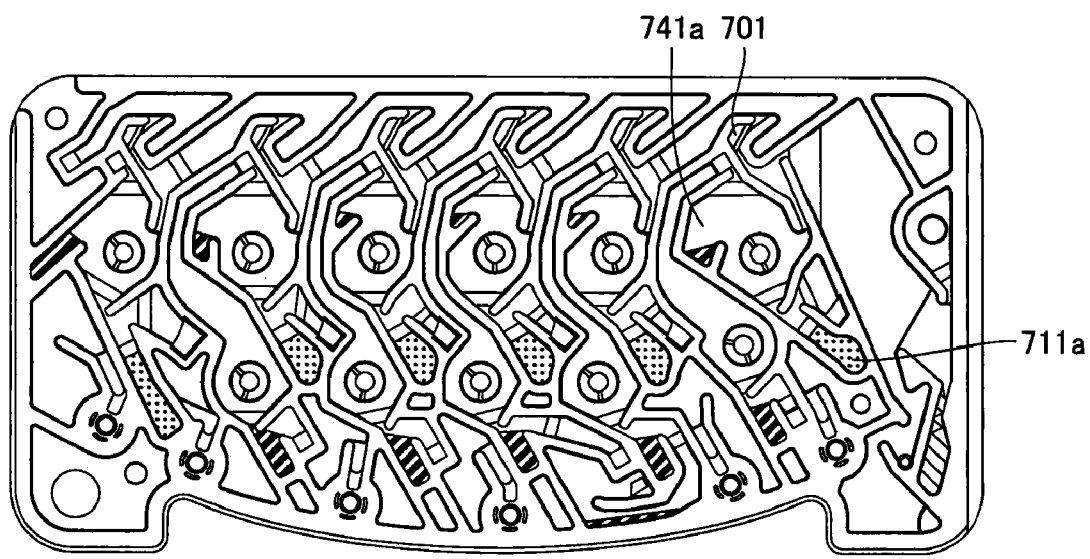

First, in this step, the centrifugal force is applied downward in FIGS. 14A and 14B (hereinafter simply referred to as downward. This is the same for FIGS. 15A, 15B, 16A, 16B, 17A, 17B, 18A, 18B, 19A, 19B, 20A, and 20B, and also the same for other directions) with respect to microchip 600 in the state shown in FIG. 12 and FIG. 13 (liquid reagent held in each liquid reagent holding portion). Thereby, a whole blood 800 introduced from specimen introducing port 620 (see FIG. 10A) of second substrate 602 moves to the lower side fluid circuit through a pass-through hole 20a, and is introduced to a blood cell separating portion 720 (see FIG. 14B). Whole blood 800 introduced to blood cell separating portion 720 is centrifugally separated in blood cell separating portion 720 by downward centrifugal force to be separated into a blood plasma component (upper layer) and a blood cell component (lower layer). Whole blood 800 overflowed from blood cell separating portion 720 when being introduced to blood cell separating portion 720 moves to the upper side fluid circuit through a pass-through hole 20b, and is accommodated in a waste storage 730 (see FIG. 14A). Further, by the application of this centrifugal force, the liquid reagents in liquid reagent holding portions 301a, 301b are passed through pass-through holes 21b, 21c to liquid reagent measuring portions 711a, 711b respectively, and then measured (see FIG. 14B). The liquid reagents overflowed from the liquid reagent measuring portions when introducing the liquid reagents into the liquid reagent measuring portions are passed through pass-through holes 21a, 21d, and accommodated in overflow reagent accommodating portions 331a, 331b of the upper side fluid circuit respectively (see FIG. 14A).

(2) Specimen Measuring Step

A leftward centrifugal force is then applied. The blood plasma component separated in blood cell separating portion 720 is thereby introduced into specimen measuring portion 701 (at the same time, introduced to specimen measuring portions 702, 703, 704, 705, and 706) and then measured (see FIG. 15B). The blood plasma component overflowed from specimen measuring portion 706 is moved into the upper side fluid circuit through a pass-through hole 26a (see FIG. 15A). The liquid reagent remains in a mixing portion 741a of the lower side fluid circuit (see FIG. 15B).

(3) First Mixing Step

A downward centrifugal force is then applied. The measured liquid reagent (liquid reagent held in liquid reagent holding portion 301a) and the blood plasma component measured in specimen measuring portion 701 are thereby mixed in liquid reagent measuring portion 711a (first step of first mixing step, see FIG. 16B).

Figure 17A:
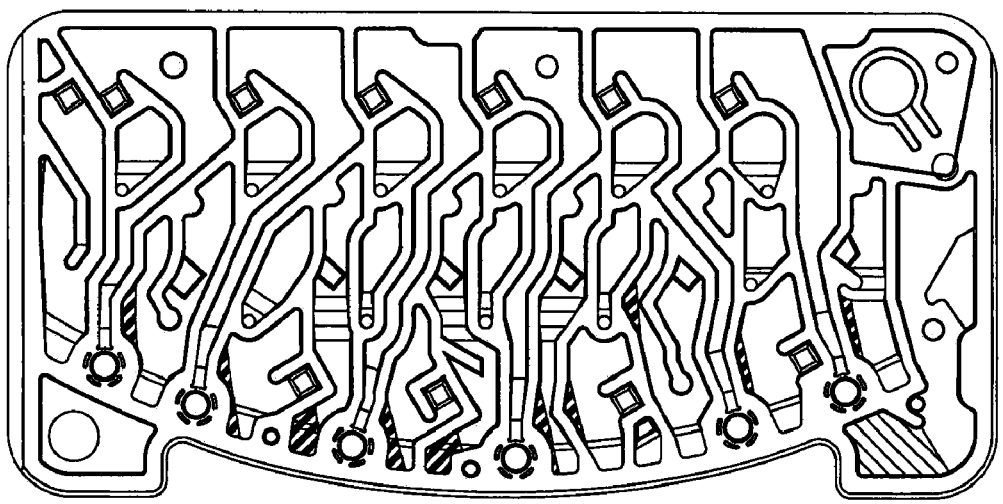
FIGS. 17A and 17B are views showing a state of liquid in the upper side fluid circuit and a state of liquid in a lower side fluid circuit in a second step of the first mixing step.
Figure 17B:
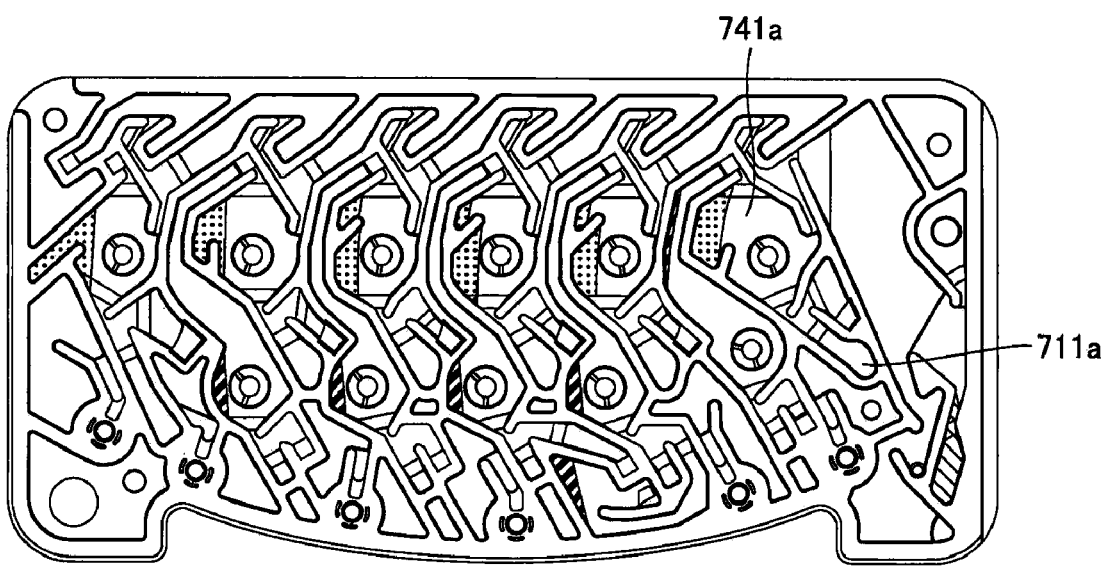
Figure 18A:
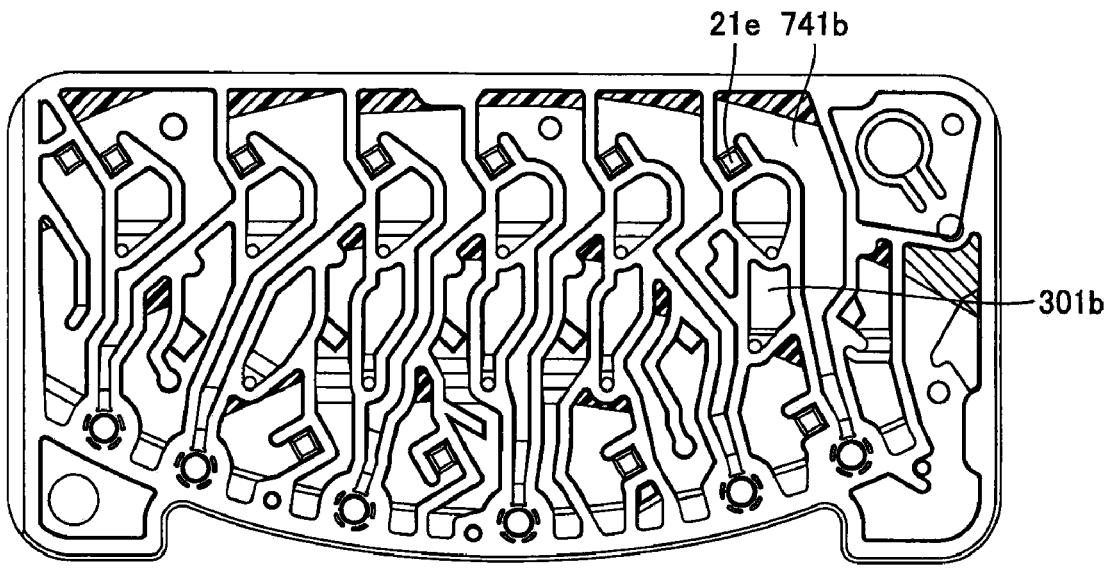
FIGS. 18A and 18B are views showing a state of liquid in an upper side fluid circuit and a state of liquid in a lower side fluid circuit in a first step of a second mixing step.
Figure 18B:
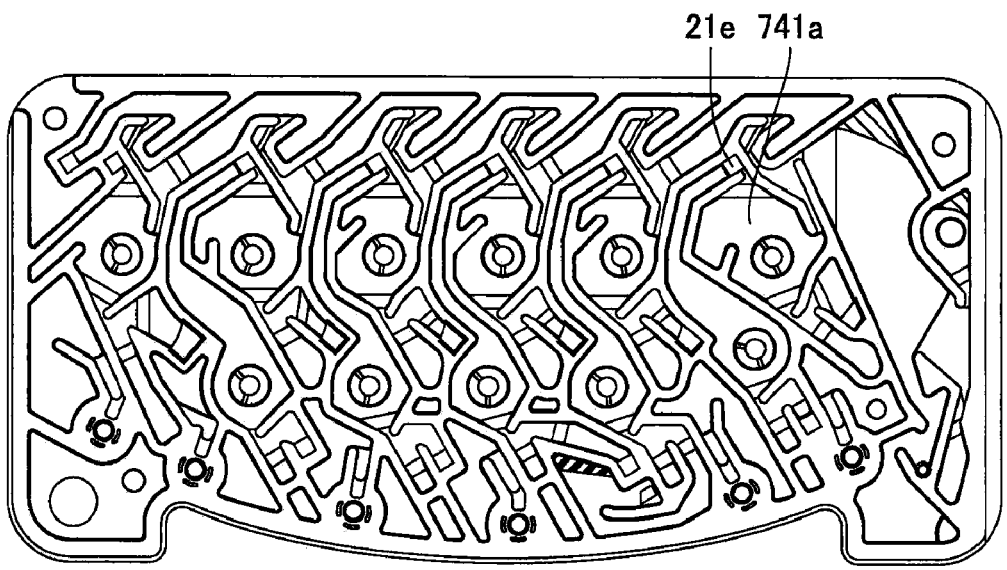

The leftward centrifugal force is then applied, so that the mixed liquid is further mixed with the liquid reagent remaining in mixing portion 741a (second step of first mixing step, see FIG. 17B). The first step and the second step are performed over a plurality of times as necessary to reliably perform mixing. The state similar to the state shown in FIGS. 17A and 17B is eventually obtained.

(4) Second Mixing Step

An upward centrifugal force is then applied. The mixed liquid in mixing portion 741a is thereby passed through a pass-through hole 21e to mixing portion 741b, and the other measured liquid reagent (liquid reagent held in liquid reagent holding portion 301b) is also passed through pass-through hole 21e to mixing portion 741b to be mixed (first step of second mixing step, see FIG. 18A).

Figure 19A:
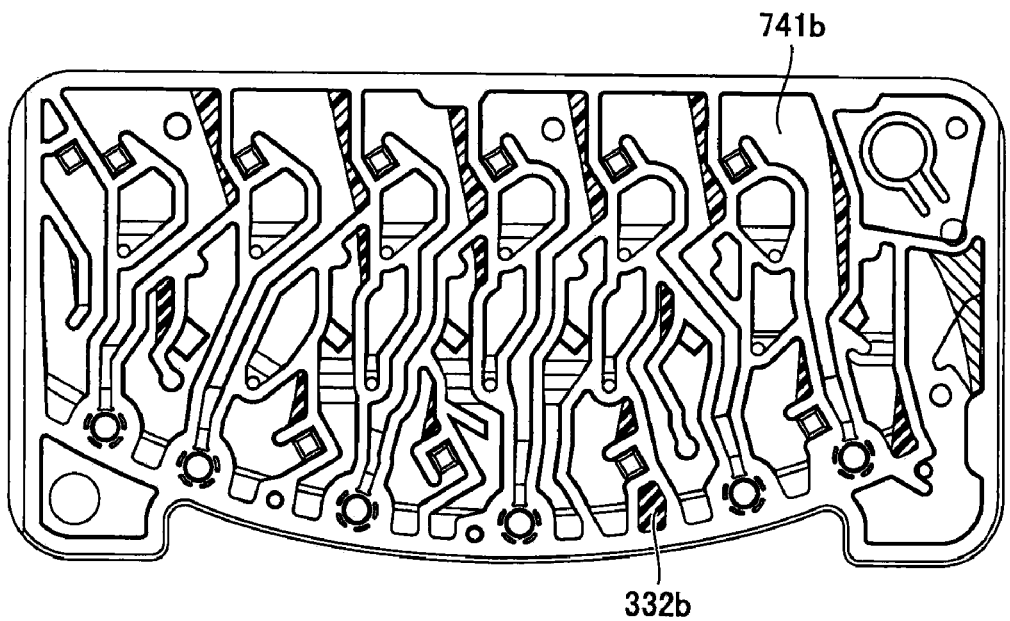
FIGS. 19A and 19B are views showing a state of liquid in the upper side fluid circuit and a state of liquid in a lower side fluid circuit in a second step of the second mixing step.
Figure 19B:
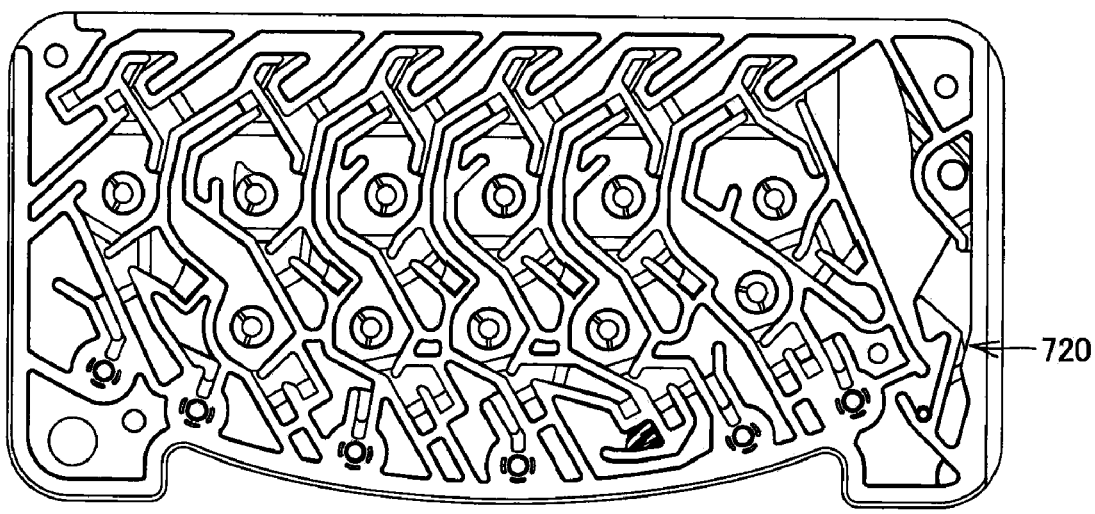
Figure 20A:
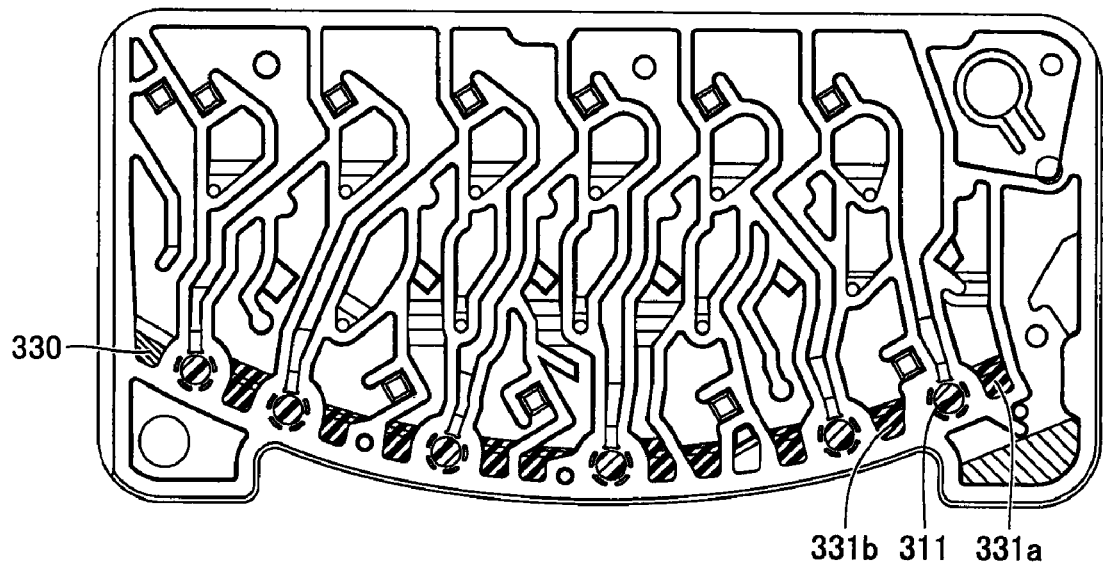
FIGS. 20A and 20B are views showing a state of liquid in the upper side fluid circuit and a state of liquid in a lower side fluid circuit in an optical measurement cuvette introducing step.
Figure 20B:
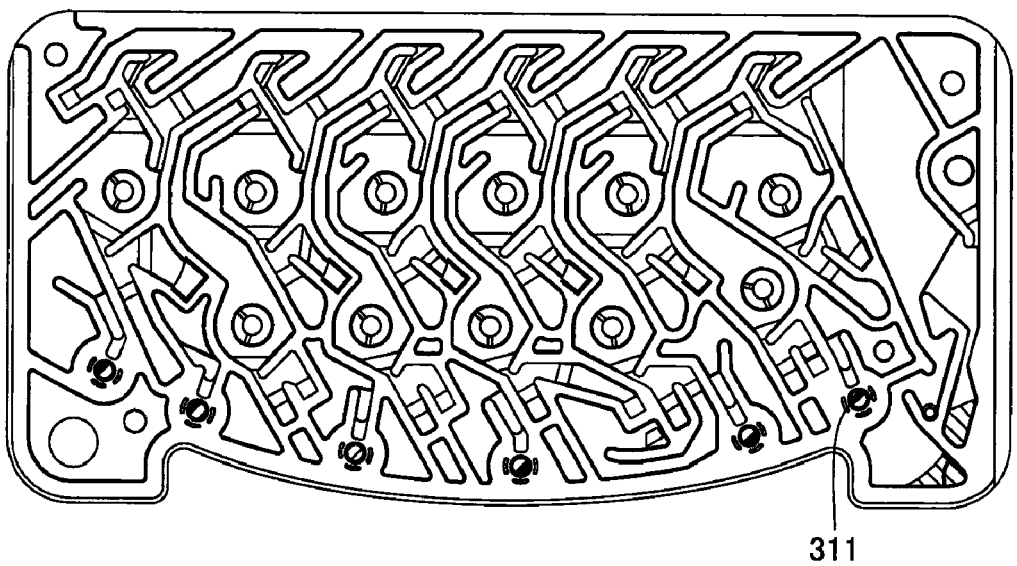

A rightward centrifugal force is then applied so that the mixed liquid moves through mixing portion 741b and the mixing is promoted, as shown in FIG. 19A (second step of second mixing step). Further, by the rightward centrifugal force, the liquid reagent is accommodated in overflow reagent accommodating portion 332b (see FIG. 19A). The first step and the second step are performed over a plurality of times as necessary to reliably perform mixing. The state similar to the state shown in FIGS. 19A and 19B is eventually obtained.

(5) Optical Measurement Cuvette Introducing Step

Finally, a downward centrifugal force is applied. The mixed liquid is thereby introduced into pass-through hole 311 configuring the optical measurement cuvette (same for other mixed liquid, see FIGS. 20A and 20B). The liquid reagent or the specimen (blood plasma component) is accommodated in overflow reagent accommodating portions 331a, 331b and overflow specimen accommodating portion 330. This is the same for other overflow reagent accommodating portions.

Through the above processing, the mixed liquid to be examined/analyzed is filled in each optical measurement cuvette, and the overflow liquid (liquid reagent or specimen) is filled in each overflow reagent accommodating portion and overflow specimen accommodating portion. In such state, through the above method, the examinations/analyses, and the detection on the presence of the overflowed liquid are conducted by irradiating the detection light from the transmitted light measurement light source and the reflected light measurement light source (which may the same light source), and rotating the first circular stage to arrange each optical measurement cuvette and each overflow liquid accommodating portion in order on the optical axis of the detection light. The check on the presence of the specimen and the liquid reagent does not necessarily need to be performed at this stage, but since the specimen and the liquid reagent are in a state accommodated in all the overflow specimen accommodating portion and the overflow reagent accommodating portions at this stage, the check on the presence of the specimen and the liquid reagent is preferably performed after the optical measurement cuvette introducing step to facilitate the operation.

The microchip according to the second embodiment of the present invention and the method of using the same have been described above using the microchip including the fluid circuit of two layers by way of example, but are not limited thereto, and the microchip may include the fluid circuit of one layer, that is, may be formed by laminating a first substrate formed with a groove and a pass-through hole configuring the fluid circuit on one side, and one second substrate that is the transparent substrate.

The number of optical measurement cuvettes of the microchip according to the second embodiment of the present invention is not particularly limited, and merely needs to be at least two or more optical measurement cuvettes. The structure of the fluid circuit is not limited to those illustrated above, and may adopt various structures according to the processing to be performed on the specimen. The fluid circuit does not necessarily need to include the overflow liquid accommodating portion, and merely needs to include at least a plurality of optical measurement cuvettes.

When the microchip according to the second embodiment of the present invention includes the fluid circuit of two layers, second substrates 602 and 603 do not necessarily need to be transparent substrates with reference to microchip 600 shown in FIGS. 10A to 10C, but at least the surface region configuring, the optical measurement cuvette needs to be transparent so that the transmitted light of the incident light can be measured. When a welding method of irradiating the laminating surface of the substrate with the light and fusing the laminating surface for lamination is used for the method of laminating first substrate 601 and second substrates 602 and 603, first substrate 601 is preferably an opaque substrate (preferably black substrate), and second substrates 602 and 603 are preferably transparent substrates so that the incident light can be more efficiently absorbed. Thereby, first substrate 601, and second substrates 602 and 603 can be easily laminated by irradiating the laminating surface of first substrate 601 with the light from second substrates 602 and 603 side, and fusing the laminating surface of first substrate 601.

Third Embodiment

Figure 21:
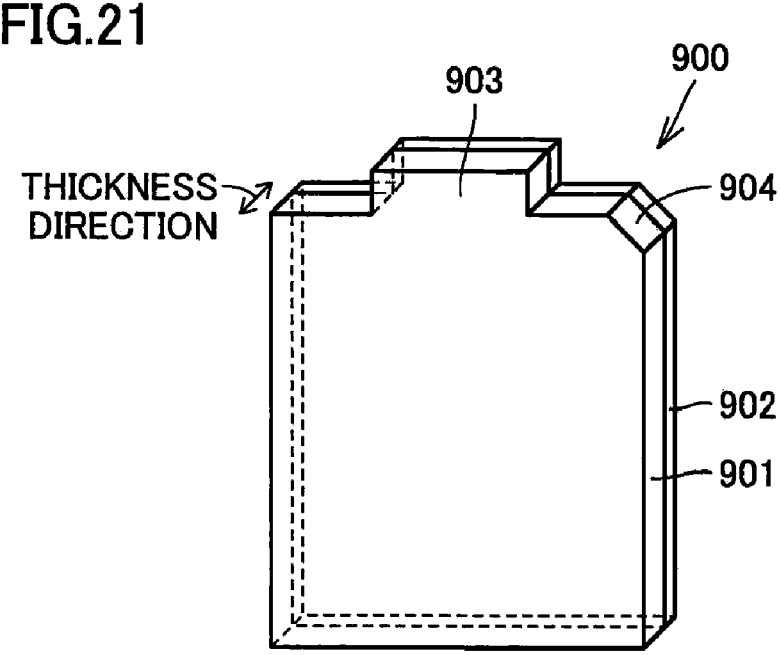
FIG. 21 is a schematic perspective view showing one example of an outer shape of a microchip according to a third embodiment of the present invention.

FIG. 21 is a schematic perspective view showing one example of an outer shape of a microchip according to a third embodiment of the present invention. A microchip 900 shown in FIG. 21 is formed by laminating two substrates of a first substrate 901 and a second substrate 902, and has a substantially flat plate shape. An optical measurement cuvette (detecting portion) for analyzing and/or examining the mixed liquid of the specimen and the liquid reagent etc., which is one part of the fluid circuit formed in the microchip is formed in a projection 903. One corner of the corners at the outer edge of microchip 900 has a cutout 904.

The microchip no longer has a symmetry plane and a symmetry center by forming cutout 904 at the outer edge of the microchip, and thus the microchip can be fitted in the correct orientation without mistaking the orientation when being fitted to the centrifugal device. Further, in manufacturing the microchip, first substrate 901 and second substrate 902 are laminated so that the cutout formed at first substrate 901 and the cutout formed at second substrate 902 match, and thus the orientation of the substrates will not be mistaken when laminating the substrates.

As shown in FIG. 21, the cutout may be formed from one surface to the other surface of the microchip, that is, over the entire thickness direction of the microchip, or may be formed at one part of the region in the thickness direction. Even in the latter case, the cutout is preferably formed at both first substrate 901 and second substrate 902 so that the orientation of the substrate is not mistaken when laminating first substrate 901 and second substrate 902.

Figure 22:
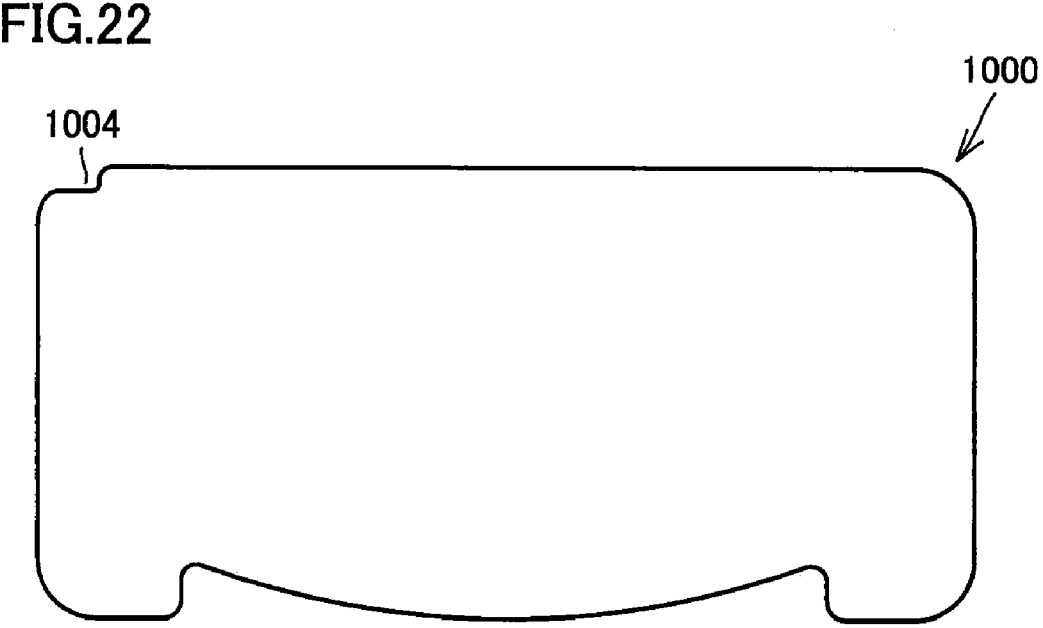
FIG. 22 is a schematic top view showing another example of the outer shape of the microchip according to the third embodiment of the present invention.

The shape of the cutout is not limited to the shape formed by diagonally cutting the corner as shown in FIG. 21, and may take various shapes. FIG. 22 is a schematic top view showing another example of the outer shape of the microchip according to the third embodiment of the present invention. A microchip 1000 shown in FIG. 22 includes a cutout 1004 at one corner, cutout 1004 being formed so that the microchip has a substantially L-shaped wall surface.

The number of corners to be formed with the cutout is not particularly limited, but it is necessary that the microchip does not have a symmetry plane or a symmetry center as a result of having a plurality of cutouts.

Figure 25:
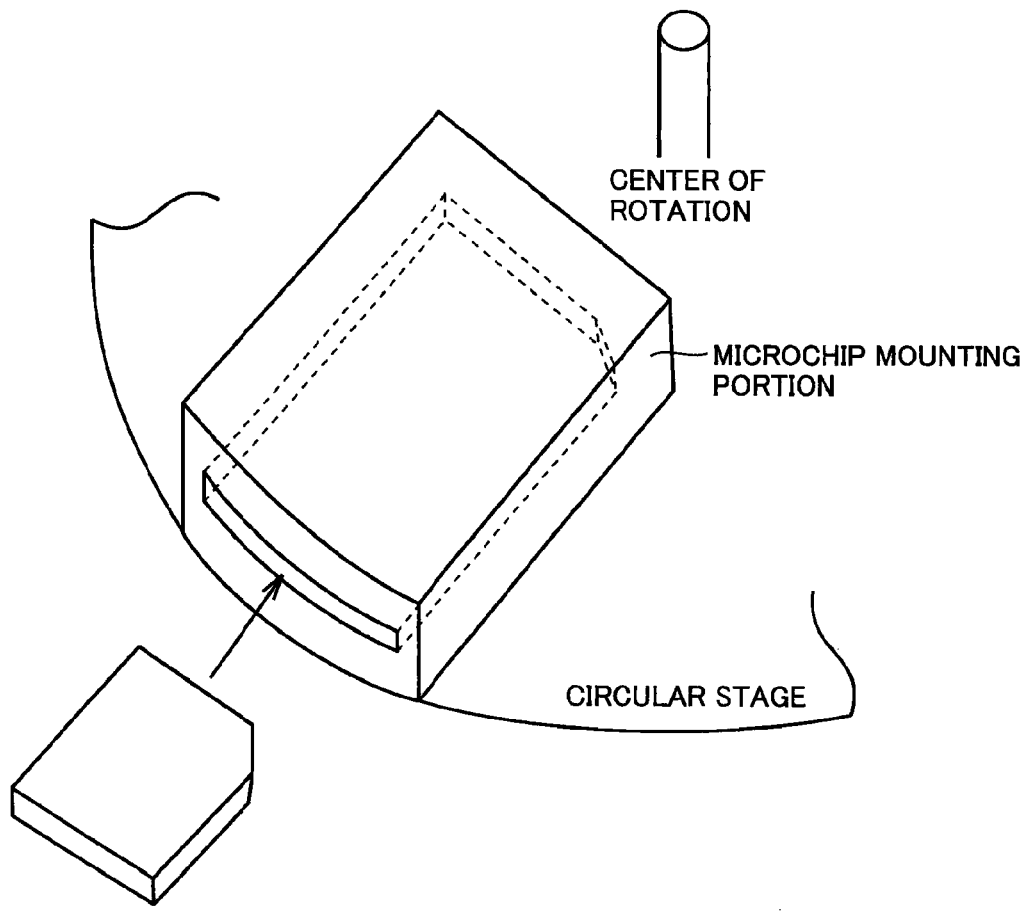
FIG. 25 is a schematic view showing a state in which a microchip is mounted on a microchip mounting portion arranged on a first or a second circular stage of the centrifugal device.
Figure 26:
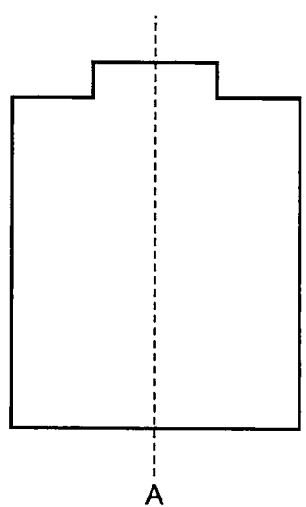
FIG. 26 is a schematic top view showing an outer shape of a conventional microchip.

The corner to be formed with the cutout of the corners at the outer edge of the microchip is not particularly limited. For instance, microchip 900 shown in FIG. 21 has six corners including the corners of projection 903, and the cutout may be formed at any one of the corners or may be formed at the corner of projection 903. The cutout is preferably formed at the corner positioned on the upstream side in the centrifugal direction of the centrifugal force applied the first on the microchip in view of the efficiency of the centrifugal operation of the microchip using the centrifugal device. That is, a plurality of corners of the microchip is roughly divided to the corner on the side (upstream side in centrifugal direction) close to a center point (centrifugal center) and the corner on the side (downstream side in centrifugal direction) distant from the center point (centrifugal center) when the microchip is mounted in the microchip mounting portion consisting of a groove for fitting the microchip or the fixed wall for supporting the mounted microchip formed on the surface of the first circular stage rotatable (revolvable) with the center point (centrifugal center) as the axis or the surface of the second circular stage for rotating the microchip arranged on the first circular stage arranged in the centrifugal device described above, but the corner including the cutout is preferably the corner on the side (upstream side in centrifugal direction) close to the center point (centrifugal center). Thus, when mounting the microchip in the microchip mounting portion consisting of the groove and the like of the first or the second stage surface, the microchip mounting portion may have a shape such that the microchip is mounted by being pushed from the outer side to the inner side of the stage, as shown in FIG. 25. The space on the stage center axis can be used as one part of the centrifugal device, thereby enhancing the degree of freedom of design of the centrifugal device. The usability of the centrifugal device and the easiness to set the microchip also can be enhanced, and the efficiency of the centrifugal operation can be achieved since the centrifugal operation can be performed without adjusting the orientation of the microchip.

Figure 23:
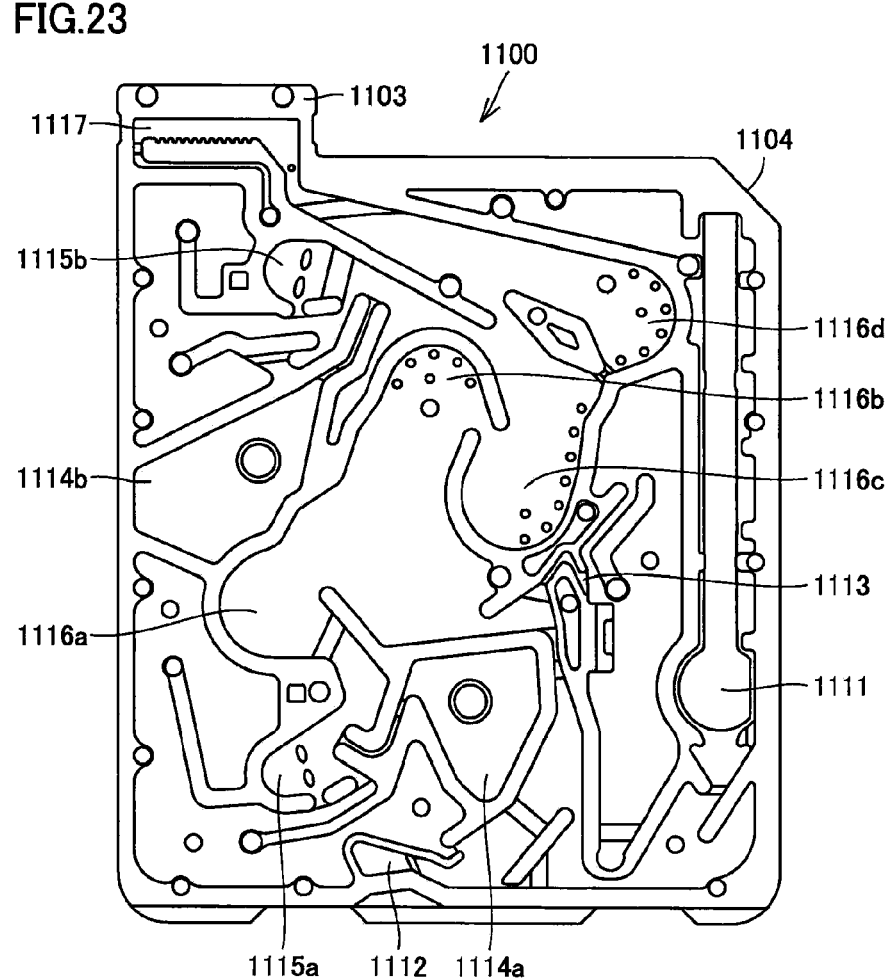
FIG. 23 is a schematic top view showing another further example of the outer shape of the microchip according to the third embodiment of the present invention.

Further advantages of forming the cutout at the corner positioned on the upstream side in the centrifugal direction of the centrifugal force applied the first on the microchip will be described using specific examples. FIG. 23 is a schematic top view showing another further example of the microchip according to the third embodiment of the present invention, and is a view showing an outer shape of the microchip and a structure of a fluid circuit formed therein. In a microchip 1100 shown in FIG. 23, a projection 1103 is arranged near the corner, different from microchip 900 of FIG. 21. A cutout 1104 is formed at one of the corners. Microchip 1110 is a chip suitably used for blood test, and a fluid circuit thereof is mainly configured by a sample tube mounting portion 1111 for incorporating a sample tube such as capillary collecting the whole blood; a blood plasma separating portion 1112 for obtaining the blood plasma component by removing the blood cell from the whole blood taken out from the sample tube; a first measuring portion 1113 for measuring the separated blood plasma component; two liquid reagent holding portions 1114a, 1114b for holding the liquid reagent; a second measuring portion 1115a and a third measuring portion 1115b for measuring the liquid reagent; mixing portions 1116a, 1116b, 1116c, and 1116d for mixing the blood plasma component and the liquid reagent; an optical measurement cuvette (detecting portion) 1117 for conducting examinations/analyses on the obtained mixed liquid; and fine fluid paths appropriately connecting such portions.

The first centrifugal operation performed on microchip 1100 is the operation of applying the downward centrifugal force in FIG. 23 to discharge the whole blood sample from the sample tube in sample tube mounting portion 1111. In this case, as shown in FIG. 23, the centrifugal operation for discharging the whole blood sample can be performed at the orientation when mounting microchip 1100 on the centrifugal device if cutout 1104 is formed at the upper right corner in microchip 1100. Therefore, the efficiency of the centrifugal operation of the microchip using the centrifugal device can be enhanced.

In the present embodiment the microchip is configured by laminating two or more substrates, where at least one of the substrates is preferably a transparent substrate and the substrate adjacent thereto is a colored substrate. For instance, if the microchip is configured by three substrates, the substrates may be in the order of transparent substrate/colored substrate/transparent substrate. According to separation by color of the substrates, the mistake in the orientation and the arrangement order when laminating the substrates, and/or the orientation of the microchip when being mounted on the centrifugal device can be avoided. The color of the colored substrate is not particularly limited, but is preferably black to satisfactorily absorb light when adhering the substrates through fusion of the substrate surfaces by light irradiation. The blackening can be carried out by adding black pigment and the like such as carbon black to the resin that is the substrate material.

Figure 24:
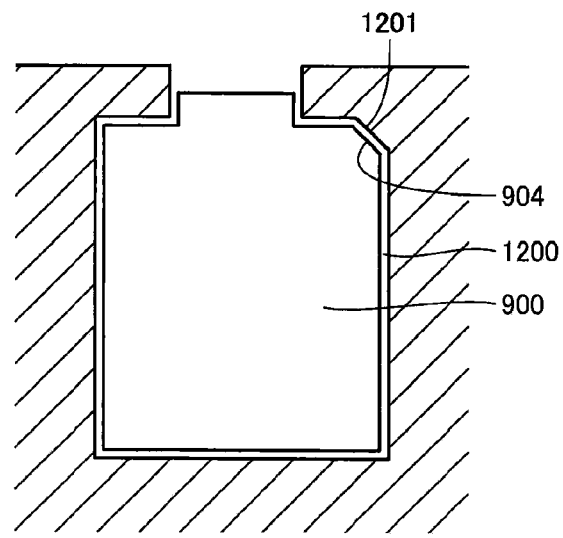
FIG. 24 is a schematic top view showing one example of a shape of a microchip mounting portion of a centrifugal device.

A projection corresponding to the shape of the cutout of the microchip is preferably arranged on the microchip mounting portion of the centrifugal device. Thus, when the microchip is inserted in the mounting portion in the wrong orientation, the projection becomes a hindrance and the microchip cannot be completely mounted in the microchip mounting portion, and thus the mistaken in orientation can be recognized. For instance, when mounting microchip 900 shown in FIG. 21 on the microchip mounting portion, a microchip mounting portion 1200 preferably includes a projection 1201 having a shape corresponding to cutout 904 of microchip 900, as shown in FIG. 24. The microchip mounting portion is not limited to being configured by the groove (concave part) and the fixed wall formed in the first or the second circular stage, and may take any mode. For instance, the microchip mounting portion may be configured by a groove (concave part) for accommodating the microchip and a lid for closing the groove, and the microchip may be accommodated in the groove through a method similar to when mounting a cassette tape to a reproducing device.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A microchip interiorly including a fluid circuit, the microchip comprising a first substrate with a groove formed on a substrate surface and a plurality of pass-through holes passing in a thickness direction of the substrate, and one or more second substrates laminated on a surface of said first substrate; wherein said fluid circuit includes:
   a liquid reagent holding portion for accommodating a liquid reagent;
   one or more measuring portions for measuring said liquid reagent or a specimen;
   one or more overflow liquid accommodating portions, connected to said measuring portion, for accommodating said liquid reagent or said specimen overflowed from said measuring portion when measuring said liquid reagent or the specimen; and
   two or more optical measurement cuvettes consisting of a space configured by one pass-through hole of said plurality of pass-through holes and a substrate surface of said second substrate;
   wherein said two or more pass-through holes configuring said optical measurement cuvettes are arranged on a circumference of a same circle at a surface of said first substrate; and
   said overflow liquid accommodating portion is arranged on a circumference arranged with said two or more pass-through holes at the surface of said first substrate.

2. The microchip according to claim 1, wherein said fluid circuit includes,
   one or more liquid reagent measuring portions for measuring said liquid reagent;
   one or more specimen measuring portions for measuring said specimen;
   two or more overflow liquid accommodating portions for accommodating said liquid reagent or said specimen overflowed from said liquid reagent measuring portion or said specimen measuring portion when measuring said liquid reagent or the specimen.

3. The microchip according to claim 1 including a first substrate with a groove formed on both surfaces of the substrate and a plurality of pass-through holes passing in the thickness direction of the substrate, and two second substrates laminated on both surfaces of said first substrate, the microchip interiorly including a fluid circuit of two layers arranged at different positions with respect to a thickness direction of the microchip.

4. The microchip according to claim 1, wherein said second substrate is a transparent substrate.

5. The microchip according to claim 1, wherein said first substrate is an opaque substrate.

6. The microchip according to claim 5, wherein said first substrate is a black substrate.

* * * * *